US012018050B2

(12) United States Patent
Agbandje-McKenna et al.

(10) Patent No.: US 12,018,050 B2
(45) **Date of Patent: *Jun. 25, 2024**

(54) AAVRH.10 VARIANTS WITH HOST ANTIBODY ESCAPE CAPABILITIES AND ALTERED TISSUE TARGETING PROPERTIES

(71) Applicant: University of Florida Research Foundation, Incorporated, Gainesville, FL (US)

(72) Inventors: Mavis Agbandje-McKenna, Gainesville, FL (US); Mario Mietzsch, Gainesville, FL (US)

(73) Assignee: University of Florida Research Foundation, Incorporated, Gainesville, FL (US)

( * ) Notice: Subject to any disclaimer, the term of this patent is extended or adjusted under 35 U.S.C. 154(b) by 175 days.

This patent is subject to a terminal disclaimer.

(21) Appl. No.: 17/359,324

(22) Filed: Jun. 25, 2021

(65) Prior Publication Data

US 2022/0017575 A1 Jan. 20, 2022

Related U.S. Application Data

(63) Continuation of application No. 16/338,397, filed as application No. PCT/US2017/054600 on Sep. 29, 2017, now Pat. No. 11,078,238.

(60) Provisional application No. 62/401,824, filed on Sep. 29, 2016.

(51) Int. Cl.

| | |
|---|---|
| *C12N 7/00* | (2006.01) |
| *C07K 14/005* | (2006.01) |
| *C12N 15/86* | (2006.01) |
| *C12N 15/85* | (2006.01) |

(52) U.S. Cl.

CPC ............ *C07K 14/005* (2013.01); *C12N 15/86* (2013.01); *C12N 2015/8518* (2013.01); *C12N 2750/14122* (2013.01); *C12N 2750/14143* (2013.01)

(58) Field of Classification Search

None

See application file for complete search history.

(56) References Cited

U.S. PATENT DOCUMENTS

| | | | |
|---|---|---|---|
| 11,078,238 | B2 | 8/2021 | Agbandje-Mckenna et al. |
| 2009/0275107 | A1 | 11/2009 | Lock et al. |
| 2013/0310443 | A1 | 11/2013 | Srivastava et al. |
| 2023/0074894 | A1 | 3/2023 | Agbandje-McKenna |

FOREIGN PATENT DOCUMENTS

| | | | |
|---|---|---|---|
| EP | 2341068 | A1 | 7/2011 |
| WO | WO 2006/110689 | A2 | 10/2006 |
| WO | WO 2013/174760 | A1 | 11/2013 |

(Continued)

OTHER PUBLICATIONS

Extended European Search Report dated Jul. 7, 2020, for Application No. EP 17857583.3.

(Continued)

*Primary Examiner* — M Franco G Salvoza

(74) *Attorney, Agent, or Firm* — Wolf, Greenfield & Sacks, P.C.

(57) ABSTRACT

This disclosure relates to variant AAVrh 10 particles engineered to escape host neutralizing antibodies but retain or improve transduction efficiency, and their use as gene delivery vehicles.

19 Claims, 24 Drawing Sheets

Specification includes a Sequence Listing.

(56) References Cited

FOREIGN PATENT DOCUMENTS

| WO | WO 2015/121501 A1 | 8/2015 |
|----|-------------------|--------|
| WO | WO 2015/168666 A2 | 11/2015 |

OTHER PUBLICATIONS

International Search Report and Written Opinion dated Mar. 9, 2018 for Application No. PCT/US2017/054600.
International Preliminary Report on Patentability dated Apr. 11, 2019 for Application No. PCT/US2017/054600.
Grosse, Small but increasingly mighty: New insights into Adeno-associated virus (AAV) capsid biology and implications for AAV vector optimization. Ph.D. Thesis submitted to the Combined faculties for the Natural Sciences and for Mathematics of the Ruperto-Carola University of Heidelberg, Germany, Apr. 22, 2016. 177 pages.
Gurda et al., Mapping a neutralizing epitope onto the capsid of adeno-associated virus serotype 8. J Virol. Aug. 2012;86(15):7739-51. doi: 10.1128/JVI.00218-12. Epub May 16, 2012.
Partial European Search Report dated Apr. 3, 2020, for Application No. EP 17857583.3.
Selot et al., 451. Successful Gene Transfer in Passively Immunized Mice with Immunologically-Inert AAVrh.10 Vectors. Mol Ther. May 1, 2015;23(S1):S179. 1 page.
Selot et al., Optimized AAV rh.10 Vectors That Partially Evade Neutralizing Antibodies during Hepatic Gene Transfer. Front Pharmacol. Jul. 17, 2017;8:441. doi: 10.3389/fphar.2017.00441.
Thwaite et al., AAVrh. 10 immunogenicity in mice and humans. Relevance of antibody cross-reactivity in human gene therapy. Gene Ther. Feb. 2015;22(2):196-201. doi: 10.1038/gt.2014.103. Epub Nov. 20, 2014.
Tseng et al., Generation and characterization of anti-Adeno-associated virus serotype 8 (AAV8) and anti-AAV9 monoclonal antibodies. J Virol Methods. Oct. 2016;236:105-110. doi: 10.1016/j.jviromet.2016.07.009. Epub Jul. 14, 2016.
Tseng et al., Mapping the AAV Capsid Host Antibody Response toward the Development of Second Generation Gene Delivery Vectors. Front Immunol. Jan. 30, 2014;5:9(1-11). doi: 10.3389/fimmu.2014.00009.
Gao et al., Adeno-associated viruses undergo substantial evolution in primates during natural infections. Proc Natl Acad Sci U S A. May 13, 2003;100(10):6081-6. doi: 10.1073/pnas.0937739100. Epub Apr. 25, 2003.
Klasse, Neutralization of Virus Infectivity by Antibodies: Old Problems in New Perspectives. Adv Biol. 2014;2014:157895. doi: 10.1155/2014/157895. Epub Sep. 9, 2014. Author Manuscript, 43 pages.
Mietsch et al., Differential adeno-associated virus serotype-specific interaction patterns with synthetic heparins and other glycans. J Virol. Mar. 2014;88(5):2991-3003. doi: 10.1128/JVI.03371-13. Epub Dec. 26, 2013.
U.S. Appl. No. 18/045,873, filed Oct. 12, 2022, Agbandje-McKenna.

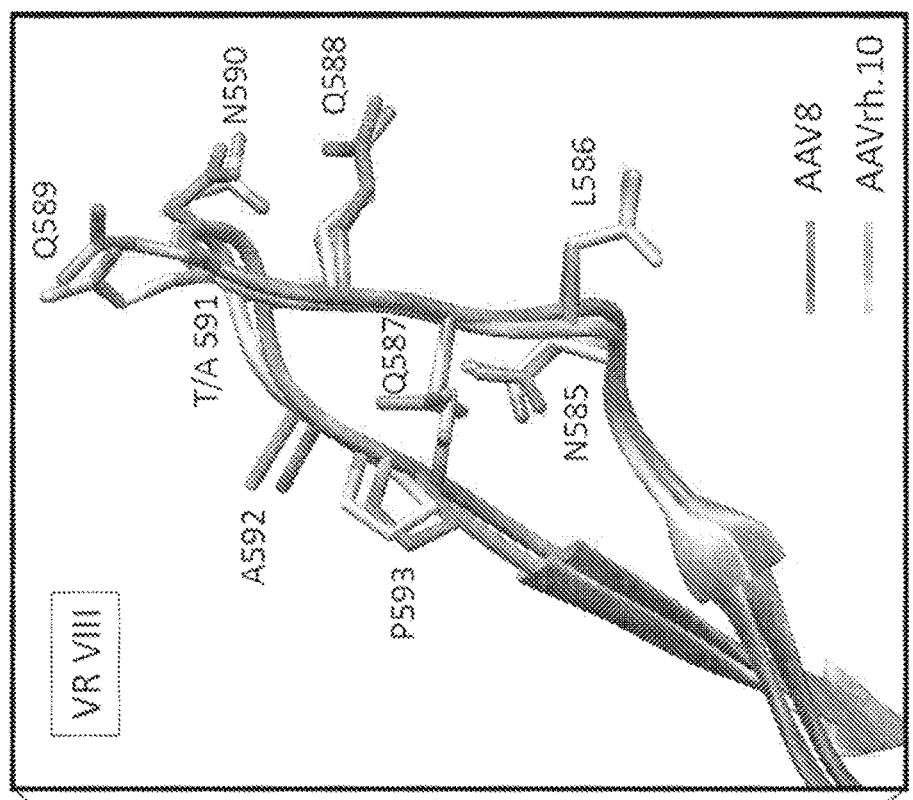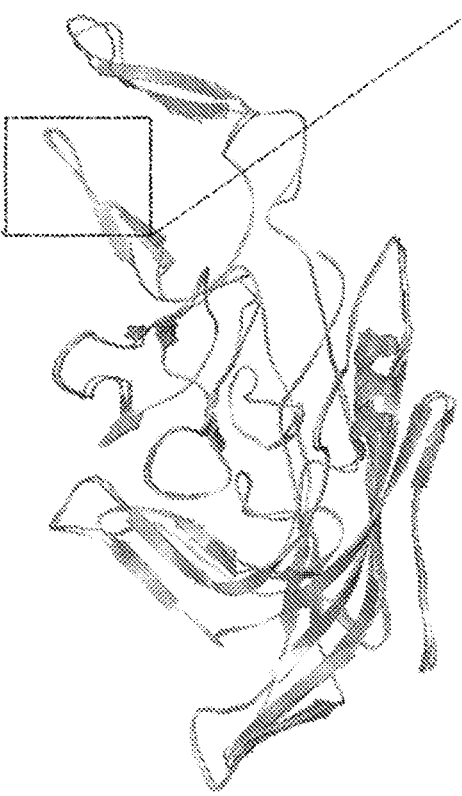
FIG. 3C

| | binder | | |
|---|---|---|---|
| AAV2 | − | NLQRGNRQA | SEQ ID NO: 3 |
| AAV3 | + | NLQSSNTAP | SEQ ID NO: 4 |
| AAV7 | + | NLQAANTAA | SEQ ID NO: 5 |
| AAV8 | + | NLQQNTAP | SEQ ID NO: 6 |
| AAVrh.10 | + | NLQQNAAP | SEQ ID NO: 7 |
| AAV13 | − | NLQNSNAGP | SEQ ID NO: 8 |
| AAV9 | − | NHQSAQAQA | SEQ ID NO: 9 |

(ADK8 label on left side)

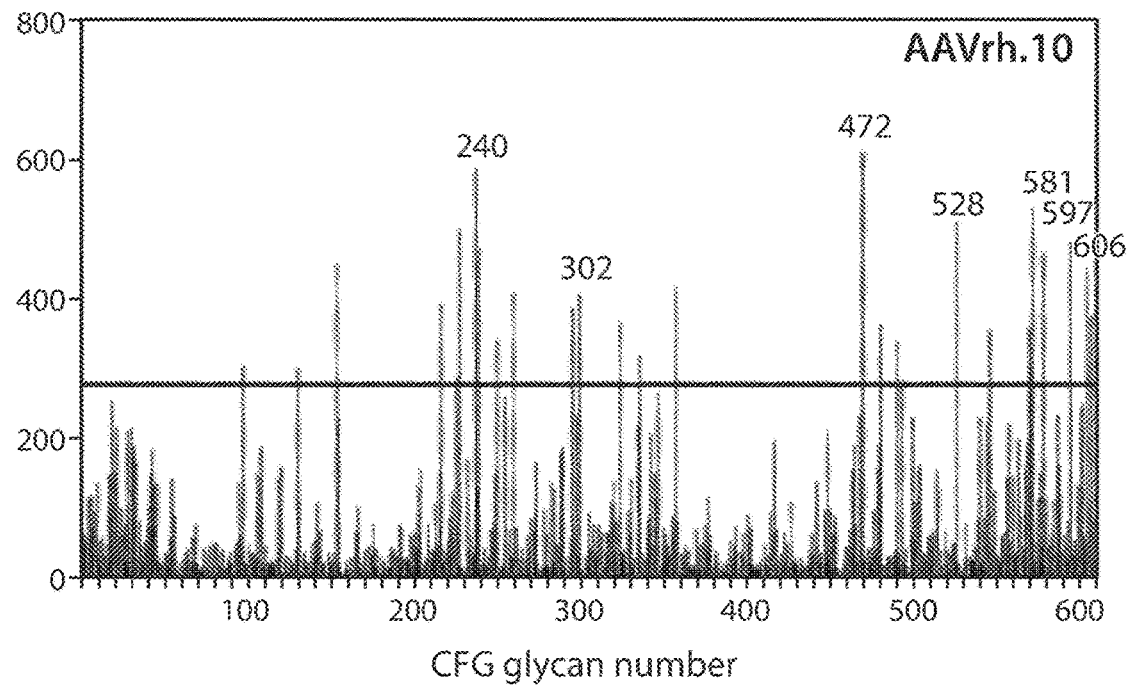
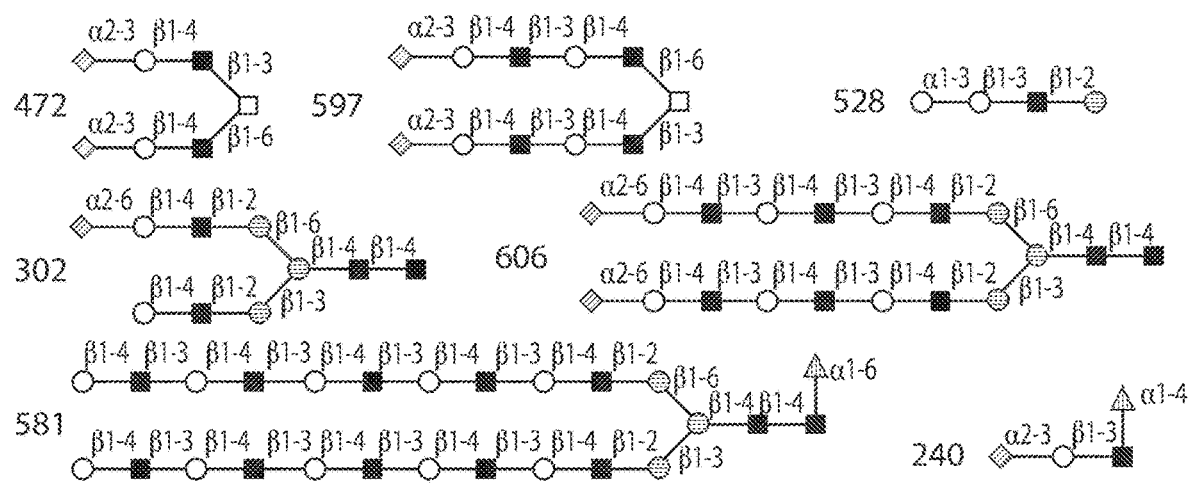
FIG. 7A

| | | |
|---|---|---|
| AAV1 | EIQYTSNYAKSANVDFTVDNNGLYTEPRPIG | SEQ ID NO: 10 |
| AAV2 | EIQYTSNYNKSVNVDFTVDTNGVYSEPRPIG | SEQ ID NO: 11 |
| AAV5 | EIQYTNNYNDPQFVDFAPDSTGEYRTTRPIG | SEQ ID NO: 12 |
| AAV8 | EIQYTSNYYKSTSVDFAVNTEGVYSEPRPIG | SEQ ID NO: 13 |
| AAV9 | EIQYTSNYYKSNNVEAVNTEGVYSEPRPIG | SEQ ID NO: 14 |
| AAVrh.10 | EIQYTSNYYKSTNVDFAVNTDGTYSEPRPIG | SEQ ID NO: 15 |

FIG. 10B

| mutation | phenotype |
|---|---|
| K259L | increased transduction efficiency compared to WT |
| ΔS453 | increased transduction efficiency compared to WT |
| S559A | increased transduction efficiency compared to WT |
| S671A | comparable tansduction compared to WT |
| T719V | increased transduction efficiency compared to WT |
| | |
| N590S / A592Q | escapes ADK8 detection |
| Q589N / N590S / A592Q | escapes ADK8 and ADK8/9 detection |

FIG. 12

| mutations | description | anticipated phenotype |
|---|---|---|
| ΔS453 + S559A + Q589N + N590S + A592Q + T719V | sextuple mutant | escapes ADK8 and ADK8/9 recognition, escape from other antibodies/IVIG, higher transduction efficiency |
| K259L + ΔS453 + S559A + Q589N + N590S + A592Q + T719V | septuple mutant | escapes ADK8 and ADK8/9 recognition, escape from other antibodies/IVIG, higher transduction efficiency |
| K333V | mutation in the DE loop | escape from antibodies/IVIG, higher transduction efficiency |
| S501A | mutation in VRV | escape from antibodies/IVIG, higher transduction efficiency |
| T674V | mutation in the HI loop | escape from antibodies/IVIG, higher transduction efficiency |

FIG. 13

| rh.10 mutation | AAV1 | AAV2 | AAV3 | AAV4 | AAV5 | AAV6 | AAV7 | AAV8 | AAV9 | AAV11 | AAV12 | AAV13 |
|---|---|---|---|---|---|---|---|---|---|---|---|---|
| K259L | K | K | K | K | R | K | K | K | K | L | L | K |
| ΔS453 | N | T | T | T | N | N | N | T | G | S | T | T |
| S559A | N | K | N | T | N | N | N | D | K | N | N | N |
| S671A | S | S | S | S | S | S | S | S | S | S | S | S |
| T719V | N | T | T | A | S | N | S | T | T | T | N | T |
| Q589N | S | G | S | N* | S | S | A | Q | A | A | A | S |
| N590S | S* | N | N | S | T | S* | N | N | Q | T | T | N |
| A592Q | D | Q* | A | L | A | D | A | A | Q* | A | A | G |
| K333V | T | T | T | T | T | T | T | K | K | T | T | T |
| S501A | S | S | S | K | S | S | S | S | S | G | G | S |
| T674V | T | T | T | T | T | T | T | T | T | T | T | T |

* same amino acid as in AAVrh.10 mutant but structurally located in a different position and / or unrelated surrounding loop sequences

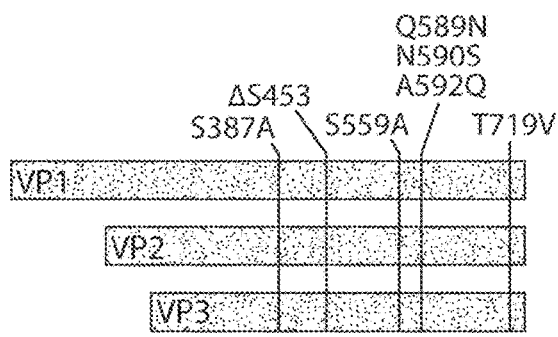
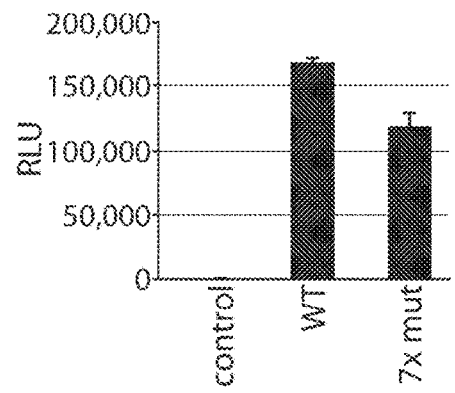
FIG. 15D
FIG. 15E
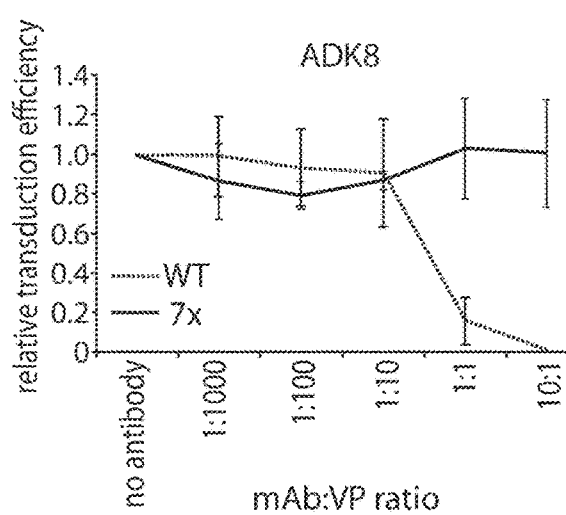
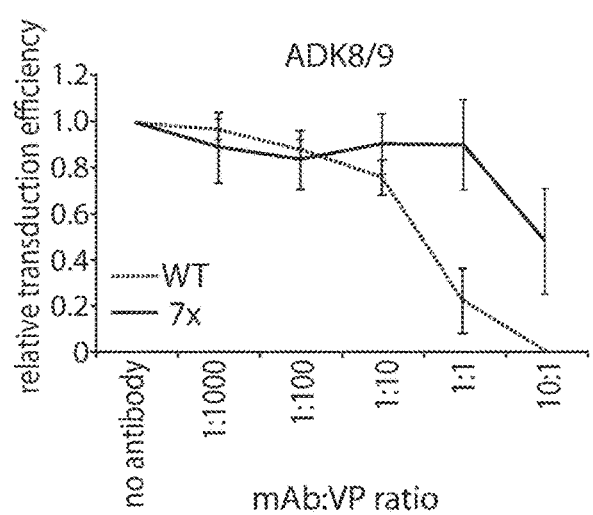
FIG. 16A
FIG. 16B

AAVRH.10 VARIANTS WITH HOST ANTIBODY ESCAPE CAPABILITIES AND ALTERED TISSUE TARGETING PROPERTIES

RELATED APPLICATIONS

This application is a continuation of U.S. application Ser. No. 16/338,397, filed Mar. 29, 2019, which is a national stage filing under 35 U.S.C. § 371 of International Patent Application Serial No. PCT/US2017/054600, filed Sep. 29, 2017, which claims the benefit of 35 U.S.C. § 119(e) of U.S. provisional application No. 62/401,824, filed Sep. 29, 2016, the contents of each of which are incorporated by reference herein in their entirety.

GOVERNMENT SUPPORT

This invention was made with government support under GM082946; awarded by the National Institutes of Health. The government has certain rights in the invention.

BACKGROUND

Adeno-associated virus (AAV) type rh.10 (AAVrh.10) was first isolated from rhesus macaque tissue (Gao et al, PNAS, 2003, 100: 6081) and is a good choice of AAV serotype for gene delivery given its capacity for high transgene expression and maintenance of copy number in both mitotic and post-mitotic tissues (De et al., Mol Ther, 2006, 13:67, and Hu et al., J Gene Med, 2010, 12: 766). AAVrh.10 is being used mostly for central nervous system targeted therapies and in a number of clinical trials as a gene delivery vehicle, for e.g., AAVrh.10-CUCLN2 in phase I/II trials for Batten disease, AAVrh.10-hARSA in phase I/II trials for Arylsulfatase A deficiency, AAVrh.10-SGSH-IRES-SUMF1 in phase I/II trials for Sanfilippo type A disease, and AAVrh.10-FIX in phase I/II trials for hemophilia B.

Antibodies against AAVrh.10 are reported to be very low in the human population (Twaite, Gene Ther, 2015, 22:196), lessening the chances of an immunogenic response in a host administered AAVrh.10 particles. However, when host neutralizing antibodies to AAVrh.10 are encountered, treatment of a disease using AAVrh.10 particles as a gene delivery vehicle can cause detrimental immunogenic effects.

SUMMARY

The inventors of this disclosure have observed that AAVrh.10 cross-reacts with anti-capsid antibodies against other AAV serotypes (e.g., AAV8) for which there is up to 40% sero-prevalence in the human population. This is likely due to the structural similarity in some surface loops between AAV8 and AAVrh.10. Patients who test positive against the AAV serotype of choice for a specific treatment have to be excluded from the cohort.

In order to circumvent the problems of antibody neutralization of AAVrh.10, the inventors of this disclosure have engineered variant recombinant AAVrh.10 particles that have one or more mutations at one or more amino acid positions in one or more capsid proteins that enable the variant particles to escape neutralizing antibodies, while retaining (e.g., at least partially), for example without diminishing, or in some embodiments, improving the transduction efficiency. Recombinant AAVrh.10 particles disclosed herein can be used in human gene delivery for patients that test positive for neutralizing antibodies against different AAV serotypes (e.g., and especially AAV8) who would otherwise be excluded from a treatment comprising AAVrh.10 particle-delivered gene therapy. The disclosed AAVrh.10 gene therapy particles that escape from preexisting antibodies against other serotypes provide an alternative serotype for the treatment of patients previously treated with an AAV of other serotypes (e.g., AAV8 in the hemophilia B trial mentioned above). These particles can also be used for treating patients previously treated with an AAVrh.10 vector, such as in the late infantile neuronal ceroid lipofuscinosis [AAVrh.10-CUCLN2], metachromatic leukodystrophy [AAVrh.10-hARSA], mucopolysaccharidosis Type IIIA disease [AAVrh.10-SGSH-IRESSUMF1], and hemophilia B [AAVrh.10-FIX] trials.

Using the disclosed variant AAVrh.10 particles that escape pre-existing antibodies in clinical trials has the potential to increase the patient cohort that can be enrolled in clinical trials, thus enabling gene therapy in a much larger percentage of the population.

This disclosure relates, at least in part, to the solution of the structure of AAVrh.10 particles and the structure-guided approach that the inventors took to engineer mutations in the capsid proteins of AAVrh.10 and an analysis of cross-reactivity antigenic epitopes. This disclosure is also based on structural mapping of LacNAc receptor binding site at the icosahedral two-fold axes on the AAVrh.10 capsid surface. The information from this mapping was used to guide the engineering of variant AAVrh.10 particles with mutations to reduce reactivity to neutralizing antibodies while avoiding mutations within the glycan binding interface. Thus, this disclosure is based on structure-based studies related to antigenic epitopes and receptor binding on the capsid to engineer AAVrh.10 particles that escape host neutralizing antibodies, while retaining (e.g., at least partially) or improving transduction efficiency and tissue tropism.

Accordingly, in some aspects, disclosed herein is a recombinant adeno-associated virus rh.10 (rAAVrh.10) particle comprising a capsid protein comprising one or more mutations. The one or more mutations may result in modulated reactivity to a neutralizing antibody and/or altered transduction efficiency of the rAAVrh.10 particle harboring the one or more mutations relative to a wild-type AAVrh.10 particle. A wild type AAVrh.10 particle may have a capsid protein with an amino acid sequence of SEQ ID NO: 2.

In some embodiments, a neutralizing antibody is against AAVrh.10. In some embodiments, a neutralizing antibody is against AAV of another serotype. AAV of another serotype may be AAV1, AAV2, AAV3, AAV4, AAV5, AAV6, AAV7, AAV8, AAV9, AAV10, AAV11, AAV12 or AAV13. In some embodiments, AAV of another serotype is AAV8. In some embodiments, a neutralizing antibody is ADK8, ADK9, IVIG, HL2381 or HL2383. In some embodiments, a neutralizing antibody is ADK8. In some embodiments, a neutralizing antibody is ADK8/9. In some embodiments, a neutralizing antibody is HL2381. In some embodiments, a neutralizing antibody is HL2383.

In some embodiments, the reactivity to neutralizing antibodies of a rAAVrh.10 particle comprising a capsid protein with one or more mutations is decreased compared to wild type AAVrh.10 particles. In some embodiments, the reactivity to neutralizing antibodies is decreased by 5-100% compared to wild type AAVrh.10 particles. In some embodiments, the reactivity to neutralizing antibodies is decreased by 70-100% compared to wild type AAVrh.10 particles.

In some embodiments, the transduction efficiency of a rAAVrh.10 particle comprising a capsid protein with one or more mutations is increased compared to wild type AAVrh.10 particles. In some embodiments, the transduction efficiency is increased by 5-200% compared to wild type AAVrh.10 particles. In some embodiments, the transduction efficiency is increased by 5-60% compared to wild type AAVrh.10 particles.

In some embodiments, the transduction efficiency of a rAAVrh.10 particle comprising a capsid protein with one or more mutations is decreased compared to wild type AAVrh.10 particles. In some embodiments, the transduction efficiency is decreased by 5-100% compared to wild type AAVrh.10 particles. In some embodiments, the transduction efficiency is decreased by 20-70% compared to wild type AAVrh.10 particles.

In some embodiments, the capsid protein which comprises one or more mutations is one or more of the capsid proteins selected from the group consisting of VP1, VP2 and VP3, (FIG. 1).

Based on the structure of AAVrh.10 capsid and alignment with AAV8, a mutation is located on a surface loop of rAAVrh.10 particle. FIG. 3A and Table 1 show the loops on the capsid surface. Accordingly in some embodiments, a mutation is at one or more amino acid positions selected from the group consisting of: K259, K333, S453, S501, S559, Q589, N590, A592, S671, T674, Y708 and T719. In some embodiments, a mutation may be a substitution (e.g., a conservative amino acid substitution, a substitution with a hydrophobic amino acid, for example A, L, or V, a substitution with a polar amino acid, for example N, S, or Q, or other amino acid substitution) or a deletion. In some embodiments, one or more mutations on a capsid protein of a rAAVrh.10 particle is selected from the group consisting of K259L, K333V, ΔS453, S501A, S559A, Q589N, N590S, A592Q, S671A, T674V, Y708A and T719V.

In some embodiments, one or more mutations on a capsid protein of a rAAVrh.10 particle is K259L. In some embodiments, one or more mutations on a capsid protein of a rAAVrh.10 particle is ΔS453. In some embodiments, one or more mutations on a capsid protein of a rAAVrh.10 particle is S559A. In some embodiments, one or more mutations on a capsid protein of a rAAVrh.10 particle is S671A. In some embodiments, one or more mutations on a capsid protein of a rAAVrh.10 particle is T719V. In some embodiments, one or more mutations on a capsid protein of a rAAVrh.10 particle are N590S and A592Q. In some embodiments, one or more mutations on a capsid protein of a rAAVrh.10 particle are Q589N, N590S and A592Q. In some embodiments, one or more mutations on a capsid protein of a rAAVrh.10 particle are ΔS453, S559A, Q589N, N590S, A592Q and T719V. In some embodiments, one or more mutations on a capsid protein of a rAAVrh.10 particle is Y708A. In some embodiments, one or more mutations on a capsid protein of a rAAVrh.10 particle are K259L, ΔS453, S559A, Q589N, N590S, A592Q and T719V. In some embodiments, one or more mutations on a capsid protein of a rAAVrh.10 particle is K333V. In some embodiments, one or more mutations on a capsid protein of a rAAVrh.10 particle is S501A. In some embodiments, one or more mutations on a capsid protein of a rAAVrh.10 particle is T674V.

The rAAVrh.10 particles were developed with the purpose of using them as gene delivery vehicles while diminishing the antigenic host response toward the particles. Accordingly, in some embodiments, a rAAVrh.10 particle comprising a capsid protein comprising one or more mutations further comprises a transgene comprising a gene of interest. In some embodiments, a gene of interest encodes a therapeutic protein. A therapeutic protein may be an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, or an anticoagulant.

In some embodiments, a gene of interest encodes a detectable molecule. In some embodiments, a rAAVrh.10 particle comprising a capsid protein comprising one or more mutations further comprises a transgene comprising more than one genes of interest. One gene of interest might encode a therapeutic protein, which another encodes a detectable molecule. In some embodiments, genes of interest comprising in a rAAVrh.10 molecule encode multiple different therapeutic proteins and/or detectable molecules.

In some embodiments, a gene of interest encodes a detectable molecule. A detectable molecule may be a fluorescent protein, a bioluminescent protein, or a protein that provides color, or a fragment thereof.

In some aspects, provided herein is a composition comprising any one of the rAAVrh.10 particles disclosed herein. In some embodiments, a composition of rAAVrh.10 particles further comprises a pharmaceutically acceptable carrier.

In some aspects, provided herein is a method of delivering a protein of interest to a subject, the method comprising administering to the subject a composition comprising any one of the rAAVrh.10 particles disclosed herein that comprise a transgene comprising a gene of interest that encodes the protein of interest.

In some aspects, provided herein is a vector that can be used to make or package any one of the rAAVrh.10 particles of this disclosure. Such a vector may comprise a nucleic acid encoding Cap proteins, wherein the Cap proteins form any one of the rAAVrh.10 particles disclosed herein.

This disclosure also provides other tools useful for the preparation or packaging of rAAVrh.10 particles in the form of a kit. Accordingly, in some aspects, provided herein is a kit comprising any one of the vectors disclosed herein, wherein the vector is contained in container. A kit may further comprise a vector comprising AAV helper genes, wherein the vector comprising the cap gene and the vector comprising AAV helper genes are provided in separate containers. In some embodiments, a kit comprises a vector comprising AAVrh.10 cap gene, a vector comprising helper genes, and packaging cells that are contained in third container. In some embodiments, AAV helper genes encode E1, E2, E4 and/or VA helper proteins.

BRIEF DESCRIPTION OF THE DRAWINGS

The following drawings form part of the present specification and are included to further demonstrate certain aspects of the present disclosure, which can be better understood by reference to one or more of these drawings in combination with the detailed description of specific embodiments presented herein. It is to be understood that the data illustrated in the drawings in no way limit the scope of the disclosure.

FIG. 2A shows an AAVrh.10 micrograph: 0.89 Å/pixel. FIG. 2B shows that AAVrh.10 exhibits the surface topology conserved in all AAVs: depressions at the 2-fold axis, cylindrical channel at the 5-fold axis, and three protrusions around the 3-fold axis.

FIGS. 3A-3C show the structural alignment of AAV8 and AAVrh.10. FIG. 3A shows the structural alignment of VP3 sequence of AAV8 versus the VP3 sequence of AAVrh.10. Capsid surface loops are circled. The VP3 sequence identity is 92.5 percent and the RMSD is 0.65 Å. The structure of VP3 shown is missing the first 15 amino acids at the N terminus. FIG. 3B shows data from an ELISA confirming the footprint of monoclonal antibody ADK8 on AAV8 (Gurda et al., JVI, 2012). FIG. 3C shows AAV8-ADK8 footprint and structure superposition of AAV8 (dark grey) and AAVrh.10 (light grey). The position of ADK8 footprint is shown in a box and enlarged to the right hand side. The amino acid positions are labeled.

FIG. 5A depicts AAVrh.10 VP protein mutations that were engineered. FIG. 5B shows amino acid sequence of the ADK8 epitope in different AAV serotypes. The + and − signs indicate AAV serotypes which can or cannot bind to ADK8, respectively. Grey highlights indicate conserved residues among AAV serotypes while boxed residues indicate residues conserved among ADK8 binders only. FIG. 5C shows the amino acid sequence of the ADK8/9 epitope in different AAV serotypes. The + and − signs indicate AAV serotypes which can or cannot bind to ADK8/9, respectively. Grey highlights indicate conserved residues among AAV serotypes while boxed residues indicate residues conserved among ADK8/9 binders. FIG. 5D shows native dot blot analysis of AAVrh.10 variants probed with the ADK8, ADK8/9, and A20 antibodies. Black dots represent recognition while blank regions indicate lack of recognition. The AAVrh.10 N590S/A592Q variant fully escapes from ADK8 and partially escapes from ADK8/9. The AAV2, AAV3 and AAV13 were used as negative control particles. A20 was used as a negative control antibody. FIG. 5E shows native dot blot analysis of AAVrh.10 variants probed with the ADK8, ADK8/9, and HL2383 antibodies. Black dots represent recognition while blank regions indicate lack of recognition. FIG. 5F shows native dot blot analysis of AAVrh.10 variants probed with the ADK8 and ADK8/9 antibodies. Black dots represent recognition while blank regions indicate lack of recognition. The AAVrh.10 Q589N/N590S/A592Q variant fully escapes from ADK8 and also escapes from ADK8/9.

FIG. 6A shows that neither heparan sulphate proteoglycans (HSPG), sialic acid nor a terminal galactose is an AAVrh.10 receptor. FIG. 6B shows data from a glycan array showing hits for AAV5 but no hits for AAVrh.10.

FIGS. 7A-7B show another analysis of the Consortium for Functional Glycomincs (CFG) glycan array data. FIG. 7A shows a more magnified view of the data depicted in FIG. 6B and the glycans that were identified using a lower threshold. FIG. 7B depicts particular glycans that were identified as binding to AAVrh.10.

FIG. 8A shows that AAVrh.10 binds to sulfated N-acetyllactosamine (LacNAc). FIG. 8B shows that 6S N-Acetyl-glucosamine is required for binding of AAVrh.10 to LacNAc.

FIG. 9A shows a cryo-EM reconstruction at 4.3 Å of AAVrh.10 capsid complexed to LacNAc glycan molecules (#6, ~1 kDa and 100 molecules per VP monomer). FIG. 9B shows the difference map obtained by subtraction of AAVrh.10 density map from glycan containing AAVrh.10 density map which revealed additional density indicated by the boxed regions at the surface of the 2-fold symmetry axes.

FIGS. 10A-10C show identification of glycan contact residues. FIG. 10A shows amino acid residues at the glycan binding site. FIG. 10B shows sequence conservation in AAV of various serotypes at the binding site. FIG. 10C shows transduction efficiency of wild type and AAVrh.10 Y708A mutant particles in cells transduced with wild type or variant/mutant AABrh.10 comprising luciferase.

FIG. 12 shows observed antibody escape and transduction efficiency phenotypes for AAVrh.10 variants.

FIG. 13 shows predicted antibody escape and transduction efficiency phenotypes for AAVrh.10 variants.

FIG. 14 provides alignment of non-limiting examples of AAVrh.10 mutations with AAV of other serotypes.

FIGS. 15A-15E show determination of the antigenicity of the AAVrh.10 capsid. FIG. 15A shows immune-dot blot analysis of native rAAV capsids of indicated serotypes. $10^{10}$ genome-containing particles were spotted on a nitrocellulose membrane. The membranes were incubated with a panel of mAbs as depicted to the left of the membrane. Monoclonal antibody B1 served as an internal loading control. FIGS. 15B and 15C show sequence alignments for the VR-VIII loop of a selection of AAV serotypes (SEQ ID NOs: 16-22 from top to bottom, respectively). Amino acids highlighted in light grey indicate sequence identity among the AAVs. In addition amino acids highlighted in darker grey indicate common residues (FIG. 15B) among the ADK8 binding AAV serotypes in the ADK8 binding epitope and (FIG. 15C) among the ADK8/9 binding AAV serotypes in the ADK8/9 binding epitope. FIG. 15D The relative positions of seven mutations (7× mut) introduced into the VP proteins of AAVrh.10 are shown. FIG. 15E Comparison of the transduction of AAVrh.10 wild-type vectors to the generated AAVrh.10 7× mutant in HEK 293 cells by a luciferase assay (MOI 100,000).

FIGS. 16A-16D show prevention of antibody-mediated AAVrh.10 neutralization. FIGS. 16A and 16B show neutralization assays using increasing amounts of purified monoclonal antibodies, ADK8 in (FIG. 16A) and ADK8/9 in (FIG. 16B) with purified AAVrh.10 wild-type (dark grey) or 7× mut (light grey) vectors carrying a luciferase gene (MOI 100,000). FIG. 16C shows a similar neutralization assay as in (FIG. 16A) except that different human serum samples were used instead of monoclonal antibodies. FIG. 16D shows native dot blot analysis using the human serum samples used in (FIG. 16C) as primary antibodies on AAV8 and AAVrh.10.

DETAILED DESCRIPTION

Not very much is known about the structure of AAVrh.10 particles. What is known is that it AAVrh.10 belongs to Glade E and is closely related to AAV8. The cap gene of AAVrh.10 is 89.2% identical to the nucleotide sequence of the cap gene of AAV8, while the encoded VP1 protein of AAVrh.10 shares 93.5% identity (and 96.2% similarity) to the VP1 protein of AAV8. Further, AAVrh.10 is not the same as AAV10. There is a 12 amino acid difference between AAVrh.10 and AAV10. FIG. 1 shows the proteins encoded by the AAVrh.10 cap gene. The AAVrh.10 cap gene encodes the capsid proteins VP1, VP2 and VP3, and assembly-activating protein (AAP). No more information about AAVrh.10 particle structure was known prior to the work carried out by the inventors of this disclosure.

To address the problem of AAVrh.10 particles reacting to host neutralizing antibodies against AAVrh.10 and AAV particles of other serotypes, the inventors first solved the AAVrh.10 capsid structure by cryo-reconstruction, and determined antibody cross-reactivity between AAVrh.10 and antibodies directed to other AAV serotypes. Antibodies against AAVrh.10 do not exist. The inventors also identified a glycan receptor involved in the cell transduction by AAVrh.10 as well as the receptor binding site on the AAVrh.10 capsid (see Examples below for data). This information was then utilized in a structure based approach, which was not possible before the work done by the inventors, to engineer mutations in the AAVrh.10 capsid that enable the variant AAVrh.10 particles to escape binding to neutralizing antibodies either without altering transduction efficiency and tissue targeting, or in some embodiments, even improve transduction efficiency.

Engineered AAVrh.10 Particles

Disclosed herein is a recombinant AAVrh.10 (rAAVrh.10) particle comprising a capsid protein comprising one or more mutations that result in modulated reactivity to neutralizing antibodies. In some embodiments, a variant recombinant AAVrh.10 particle as disclosed herein comprises mutations that result in altered transduction efficiency. In some embodiments, mutations in the capsid protein of AAVrh.10 particles results in both modulated reactivity to neutralizing antibodies and altered transduction efficiency.

As described herein, variant AAVrh.10 particles are those that have an amino acid sequence that is different from the sequence of wild-type AAVrh.10 particles. The term "engineered" is used synonymously with the term "recombinant." The term "variant" as used herein means different from wild type. A wild type AAVrh.10 particle may be one found in nature or a recombinant viral particle that is made in a laboratory setting for the purpose of testing phenotypes. A variant AAVrh.10 particle as used herein is one that is engineered.

Figure 1:
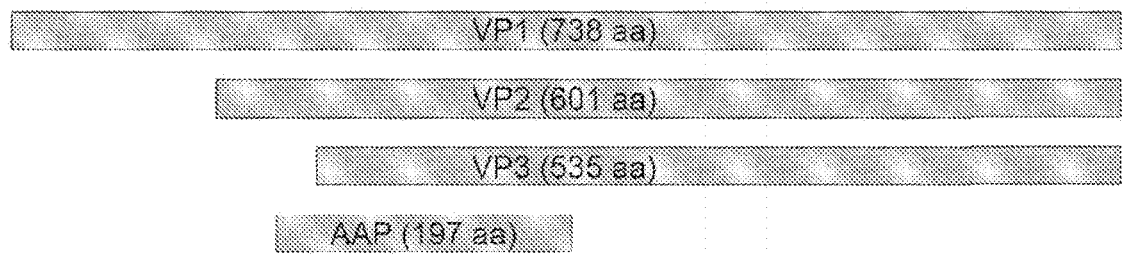
FIG. 1 shows a depiction of the AAVrh.10 VP proteins encoded by the cap gene.

In some embodiments, the difference in amino acid sequence is present in one or more capsid proteins (e.g., VP1, VP2, VP3, VP1 and VP2, or VP1, VP2 and VP3). The AAV genome encodes overlapping sequences of the three capsid proteins, VP1, VP2 and VP3, which starts from one promoter. All three of the proteins are translated from one mRNA. After the mRNA is synthesized, it can be spliced in different ways, resulting in expression of the three proteins VP1, VP2 and VP3 (FIG. 1). The difference between the amino acid sequence between a "variant" AAVrh.10 particle and a wild type particle may be in one or more amino acids. For example, a variant AAVrh.10 may contain only 1 or 2, 3, 4, 5, 6, or 7 or more mutations compared to the amino acid sequence of wild type AAVrh.10. The nucleic acid encoding, and the amino acid sequence of wild type AAVrh.10 capsid proteins are provided as SEQ ID NOs: 1 and 2, respectively. Table 1 provides amino acid sequence limitations for the VP1, VP2 and VP3 capsid proteins.

```
Nucleic acid sequence of the cap gene for wild-type AAVrh.10
                                                  (SEQ ID NO: 1)
ATGGCTGCCGATGGTTATCTTCCAGATTGGCTCGAGGACAACCTCTCTGAGGGCATTCGCGAGT

GGTGGGACTTGAAACCTGGAGCCCCGAAACCCAAAGCCAACCAGCAAAAGCAGGACGACGGCCG

GGGTCTGGTGCTTCCTGGCTACAAGTACCTCGGACCCTTCAACGGACTCGACAAGGGGGAGCCC

GTCAACGCGGCGGACGCAGCGGCCCTCGAGCACGACAAGGCCTACGACCAGCAGCTCAAAGCGG

GTGACAATCCGTACCTGCGGTATAACCACGCCGACGCCGAGTTTCAGGAGCGTCTGCAAGAAGA

TACGTCTTTTGGGGGCAACCTCGGGCGAGCAGTCTTCCAGGCCAAGAAGCGGGTTCTCGAACCT

CTCGGTCTGGTTGAGGAAGGCGCTAAGACGGCTCCTGGAAAGAAGAGACCGGTAGAGCCATCAC

CCCAGCGTTCTCCAGACTCCTCTACGGGCATCGGCAAGAAAGGCCAGCAGCCCGCGAAAAAGAG

ACTCAACTTTGGGCAGACTGGCGACTCAGAGTCAGTGCCCGACCCTCAACCAATCGGAGAACCC

CCCGCAGGCCCCTCTGGTCTGGGATCTGGTACAATGGCTGCAGGCGGTGGCGCTCCAATGGCAG

ACAATAACGAAGGCGCCGACGGAGTGGGTAGTTCCTCAGGAAATTGGCATTGCGATTCCACATG

GCTGGGCGACAGAGTCATCACCACCAGCACCCGAACCTGGGCCCTCCCCACCTACAACAACCAC

CTCTACAAGCAAATCTCCAACGGGACTTCGGGAGGAAGCACCAACGACAACACCTACTTCGGCT

ACAGCACCCCCTGGGGGTATTTTGACTTTAACAGATTCCACTGCCACTTCTCACCACGTGACTG

GCAGCGACTCATCAACAACAACTGGGGATTCCGGCCCAAGAGACTCAACTTCAAGCTCTTCAAC

ATCCAGGTCAAGGAGGTCACGCAGAATGAAGGCACCAAGACCATCGCCAATAACCTTACCAGCA

CGATTCAGGTCTTTACGGACTCGGAATACCAGCTCCCGTACGTCCTCGGCTCTGCGCACCAGGG

CTGCCTGCCTCCGTTCCCGGCGGACGTCTTCATGATTCCTCAGTACGGGTACCTGACTCTGAAC
```

-continued

```
AATGGCAGTCAGGCCGTGGGCCGTTCCTCCTTCTACTGCCTGGAGTACTTTCCTTCTCAAATGC

TGAGAACGGGCAACAACTTTGAGTTCAGCTACCAGTTTGAGGACGTGCCTTTTCACAGCAGCTA

CGCGCACAGCCAAAGCCTGGACCGGCTGATGAACCCCCTCATCGACCAGTACCTGTACTACCTG

TCTCGGACTCAGTCCACGGGAGGTACCGCAGGAACTCAGCAGTTGCTATTTTCTCAGGCCGGGC

CTAATAACATGTCGGCTCAGGCCAAAAACTGGCTACCCGGGCCCTGCTACCGGCAGCAACGCGT

CTCCACGACACTGTCGCAAAATAACAACAGCAACTTTGCCTGGACCGGTGCCACCAAGTATCAT

CTGAATGGCAGAGACTCTCTGGTAAATCCCGGTGTCGCTATGGCAACCCACAAGGACGACGAAG

AGCGATTTTTTCCGTCCAGCGGAGTCTTAATGTTTGGGAAACAGGGAGCTGGAAAAGACAACGT

GGACTATAGCAGCGTTATGCTAACCAGTGAGGAAGAAATTAAAACCACCAACCCAGTGGCCACA

GAACAGTACGGCGTGGTGGCCGATAACCTGCAACAGCAAACGCCGCTCCTATTGTAGGGGCCG

TCAACAGTCAAGGAGCCTTACCTGGCATGGTCTGGCAGAACCGGGACGTGTACCTGCAGGGTCC

TATCTGGGCCAAGATTCCTCACACGGACGGAAACTTTCATCCCTCGCCGCTGATGGGAGGCTTT

GGACTGAAACACCCGCCTCCTCAGATCCTGATTAAGAATACACCTGTTCCCGCGGATCCTCCAA

CTACCTTCAGTCAAGCTAAGCTGGCGTCGTTCATCACGCAGTACAGCACCGGACAGGTCAGCGT

GGAAATTGAATGGGAGCTGCAGAAAGAAAACAGCAAACGCTGGAACCCAGAGATTCAATACACT

TCCAACTACTACAAATCTACAAATGTGGACTTTGCTGTTAACACAGATGGCACTTATTCTGAGC

CTCGCCCCATCGGCACCCGTTACCTCACCCGTAATCTGTAA

Amino acid sequence of the capsid protein for wild-type AAVrh.10
                                                  (SEQ ID NO: 2)
MAADGYLPDWLEDNLSEGIREWWDLKPGAPKPKANQQKQDDGRGLVLPGYKYLGPFNGLDKGEP

VNAADAAALEHDKAYDQQLKAGDNPYLRYNHADAEFQERLQEDTSFGGNLGRAVFQAKKRVLEP

LGLVEEGAKTAPGKKRPVEPSPQRSPDSSTGIGKKGQQPAKKRLNFGQTGDSESVPDPQPIGEP

PAGPSGLGSGTMAAGGGAPMADNNEGADGVGSSSGNWHCDSTWLGDRVITTSTRTWALPTYNNH

LYKQISNGTSGGSTNDNTYFGYSTPWGYFDFNRFHCHFSPRDWQRLINNNWGFRPKRLNFKLFN

IQVKEVTQNEGTKTIANNLTSTIQVFTDSEYQLPYVLGSAHQGCLPPFPADVFMIPQYGYLTLN

NGSQAVGRSSFYCLEYFPSQMLRTGNNFEFSYQFEDVPFHSSYAHSQSLDRLMNPLIDQYLYYL

SRTQSTGGTAGTQQLLFSQAGPNNMSAQAKNWLPGPCYRQQRVSTTLSQNNNSNFAWTGATKYH

LNGRDSLVNPGVAMATHKDDEERFFPSSGVLMFGKQGAGKDNVDYSSVMLTSEEEIKTTNPVAT

EQYGVVADNLQQQNAAPIVGAVNSQGALPGMVWQNRDVYLQGPIWAKIPHTDGNFHPSPLMGGF

GLKHPPPQILIKNTPVPADPPTTFSQAKLASFITQYSTGQVSVEIEWELQKENSKRWNPEIQYT

SNYYKSTNVDFAVNTDGTYSEPRPIGTRYLTRNL
```

An AAVrh.10 particle may be an empty capsid, or an AAV particle comprising nucleic acid.

Figures 5A, 5B:
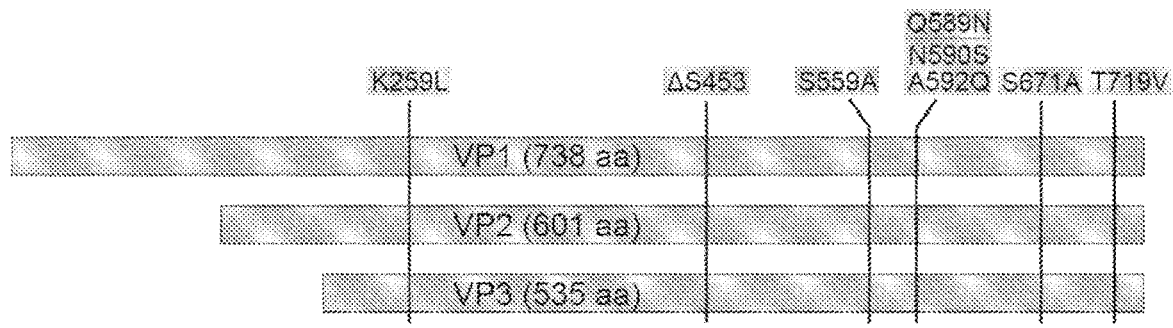
FIGS. 5A-5F show antibody escape phenotypes of AAVrh.10 variants.
Figures 5C, 5D:
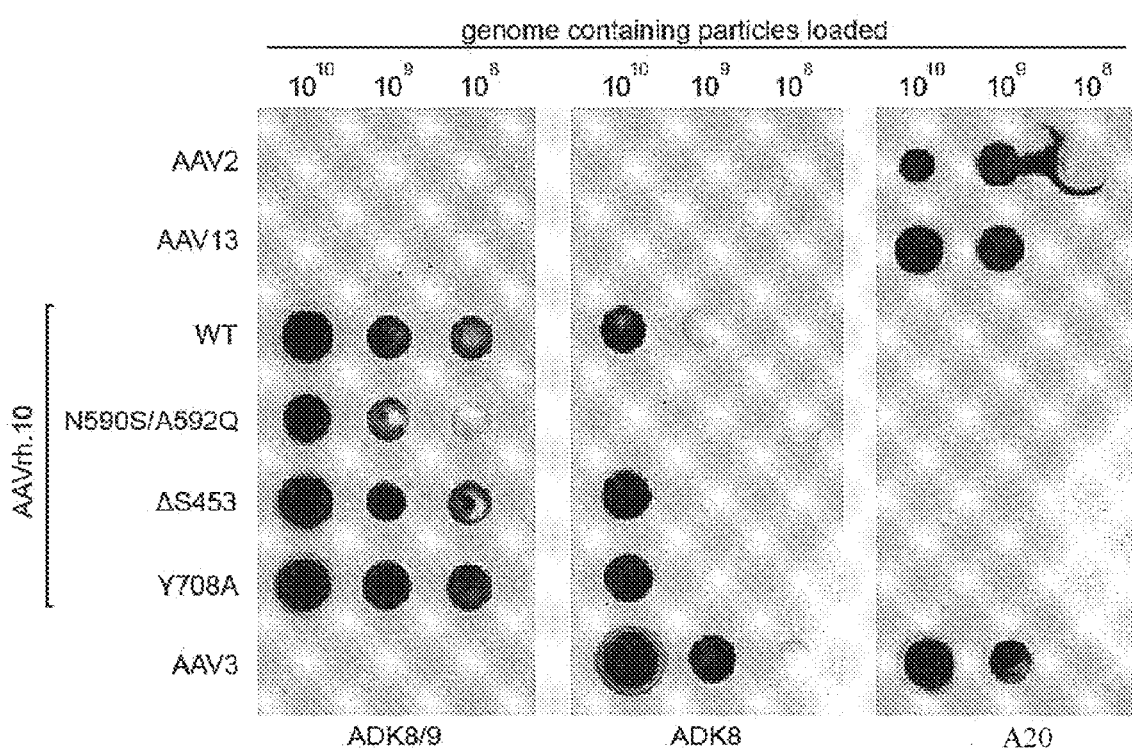
Figure 5E:
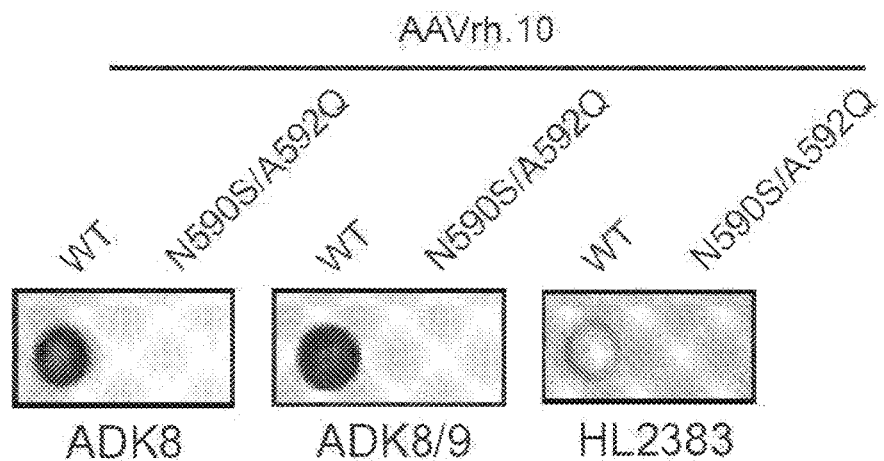
Figure 5F:
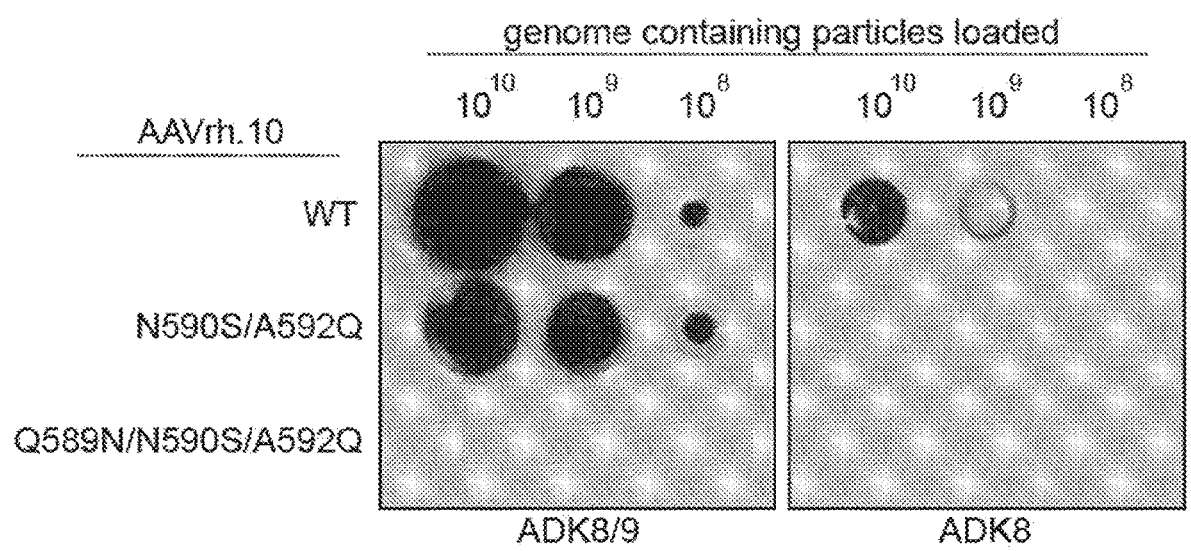
Figure 6A:
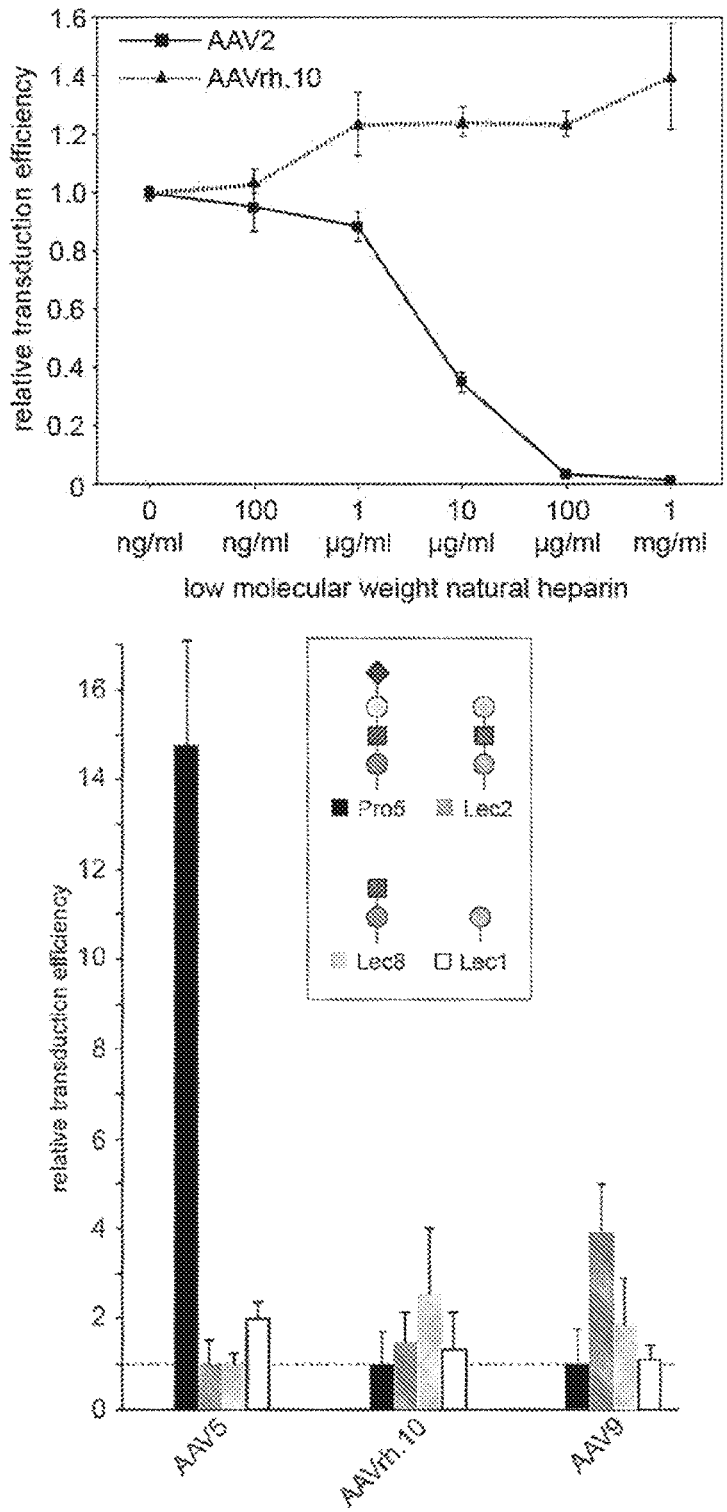
FIGS. 6A-6B show data from an experiment to identify a receptor that binds to AAVrh.10 (Mietzch et al., JVI, 2014).
Figure 6B:
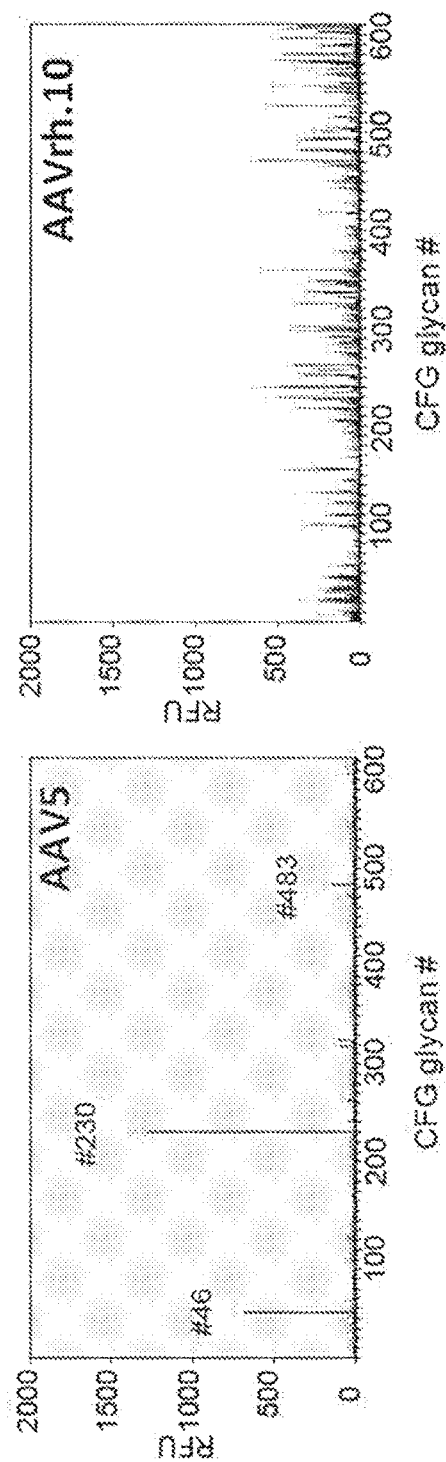
Figure 7B:
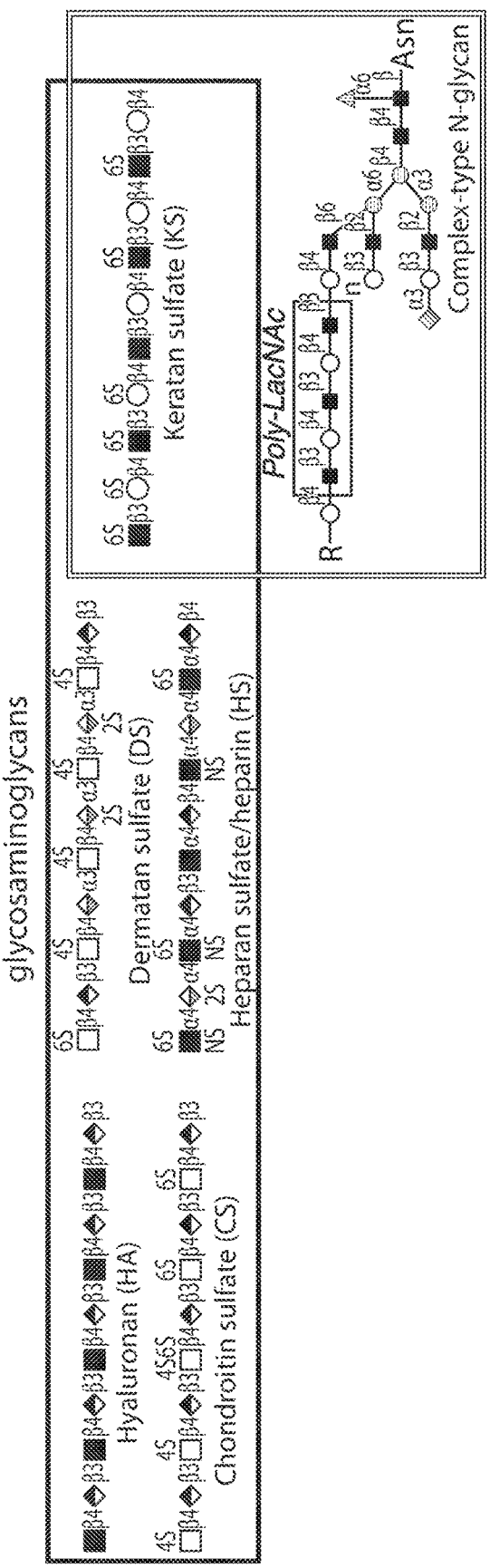
Figure 8A:
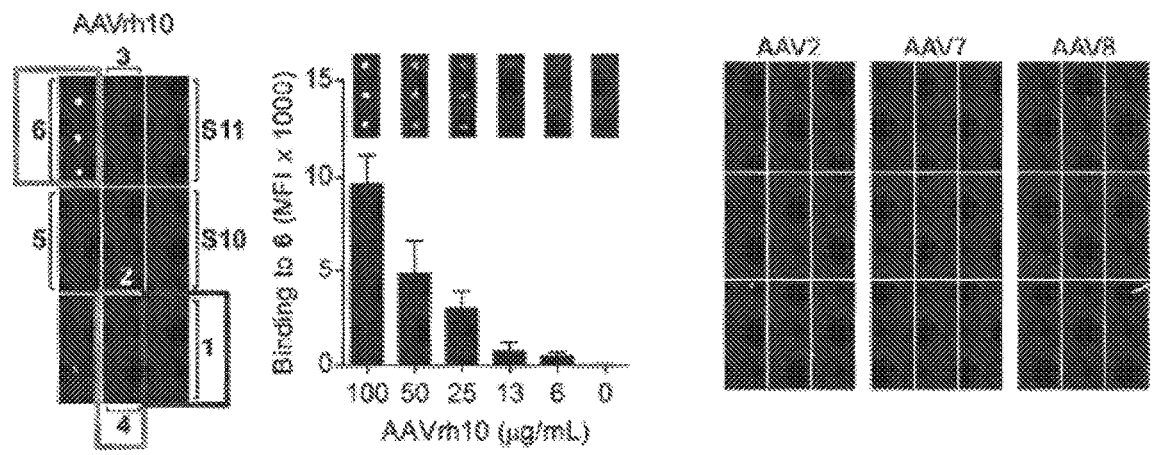
FIGS. 8A-8B show screening of AAVs on a LacNAc glycan array.
Figure 8B:
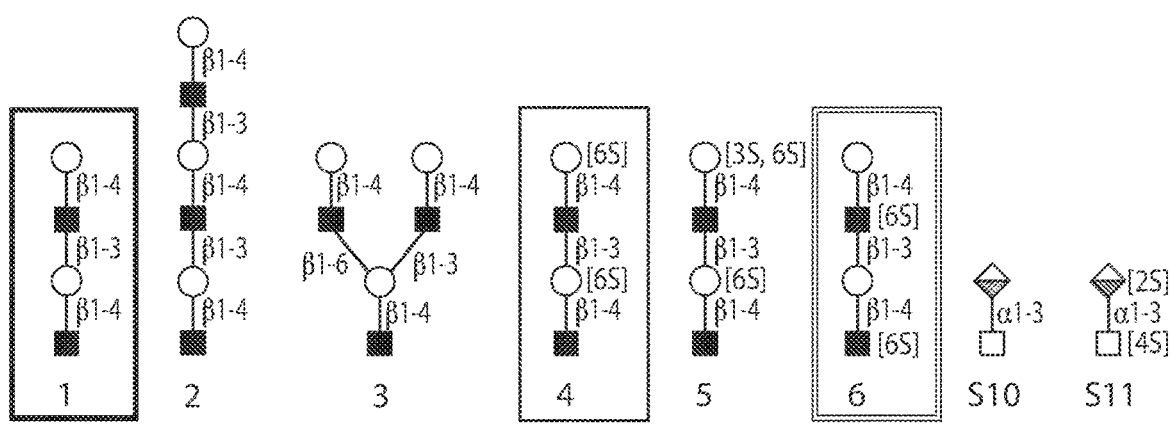
Figure 9A:
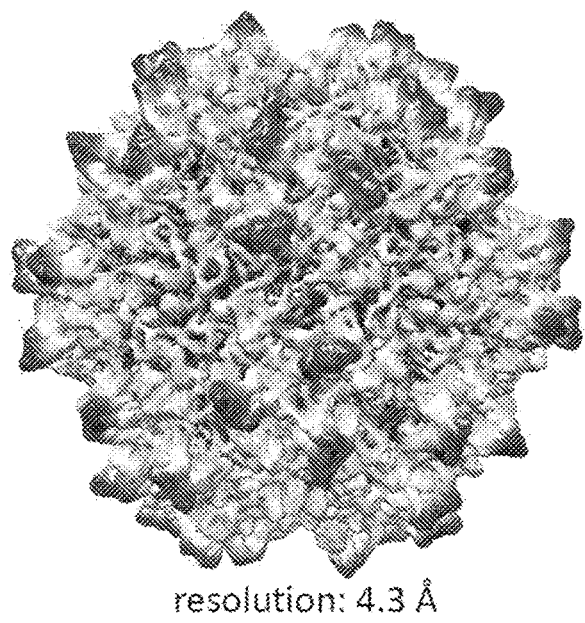
FIGS. 9A-9B show identification of the glycan binding site on AAVrh.10 capsid by cryo-EM reconstruction.
Figure 9B:
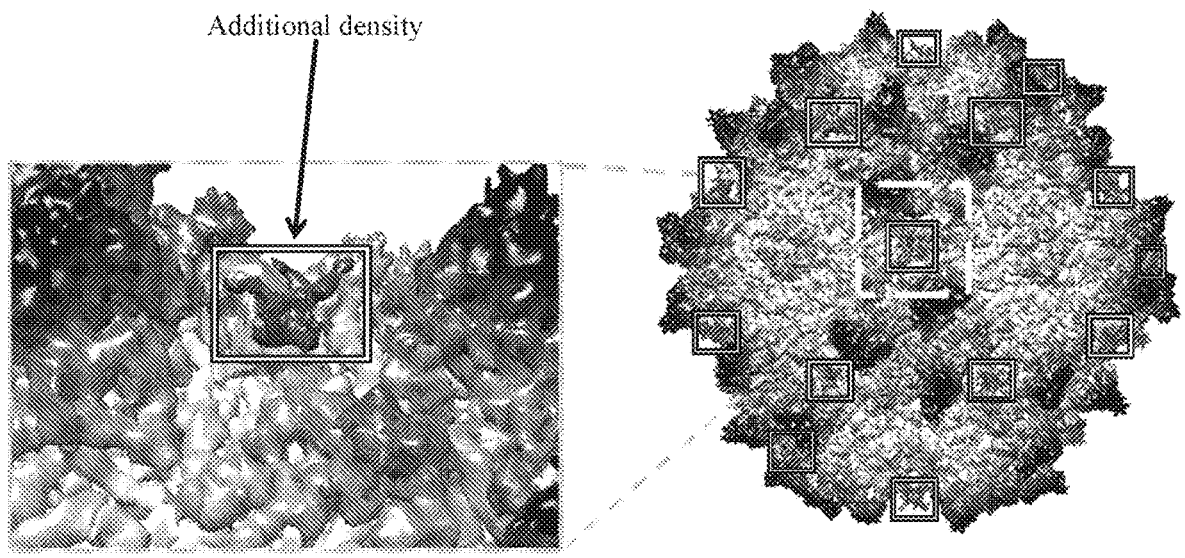
Figure 10A:
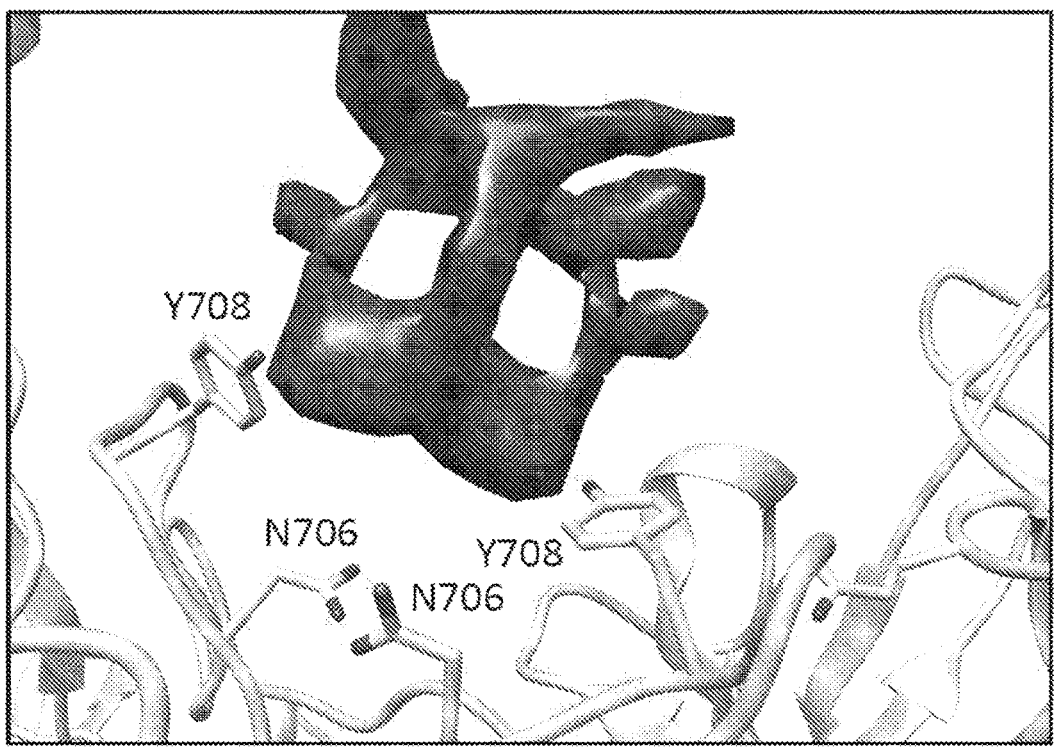
Figure 10C:
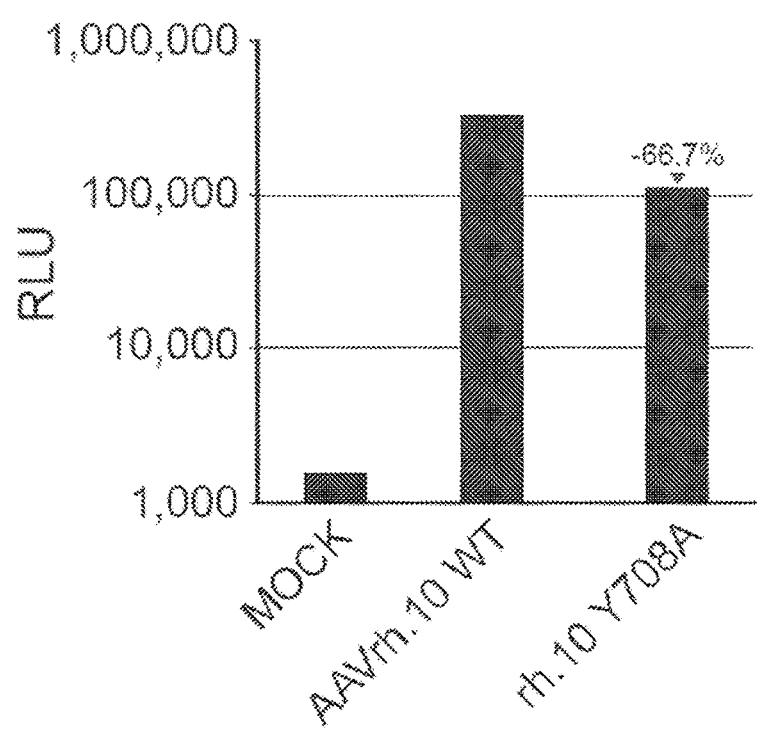
Figure 11:
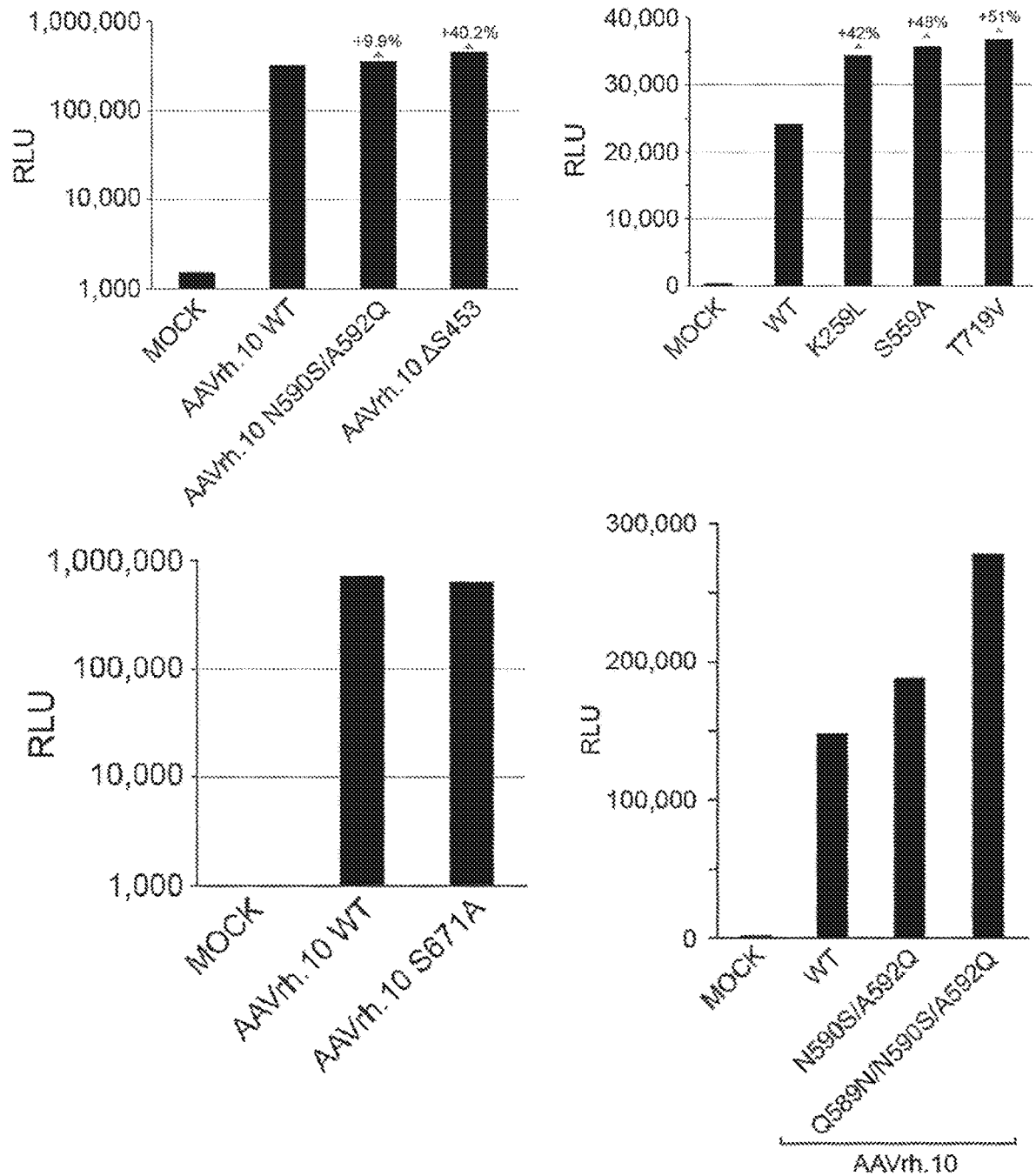
FIG. 11 shows transduction efficiency of engineered AAVrh.10 variants measured based on luciferase expression. Variants show increased transduction efficiency compared to wild-type (WT) AAVrh.10.
Figures 15A, 15B, 15C:
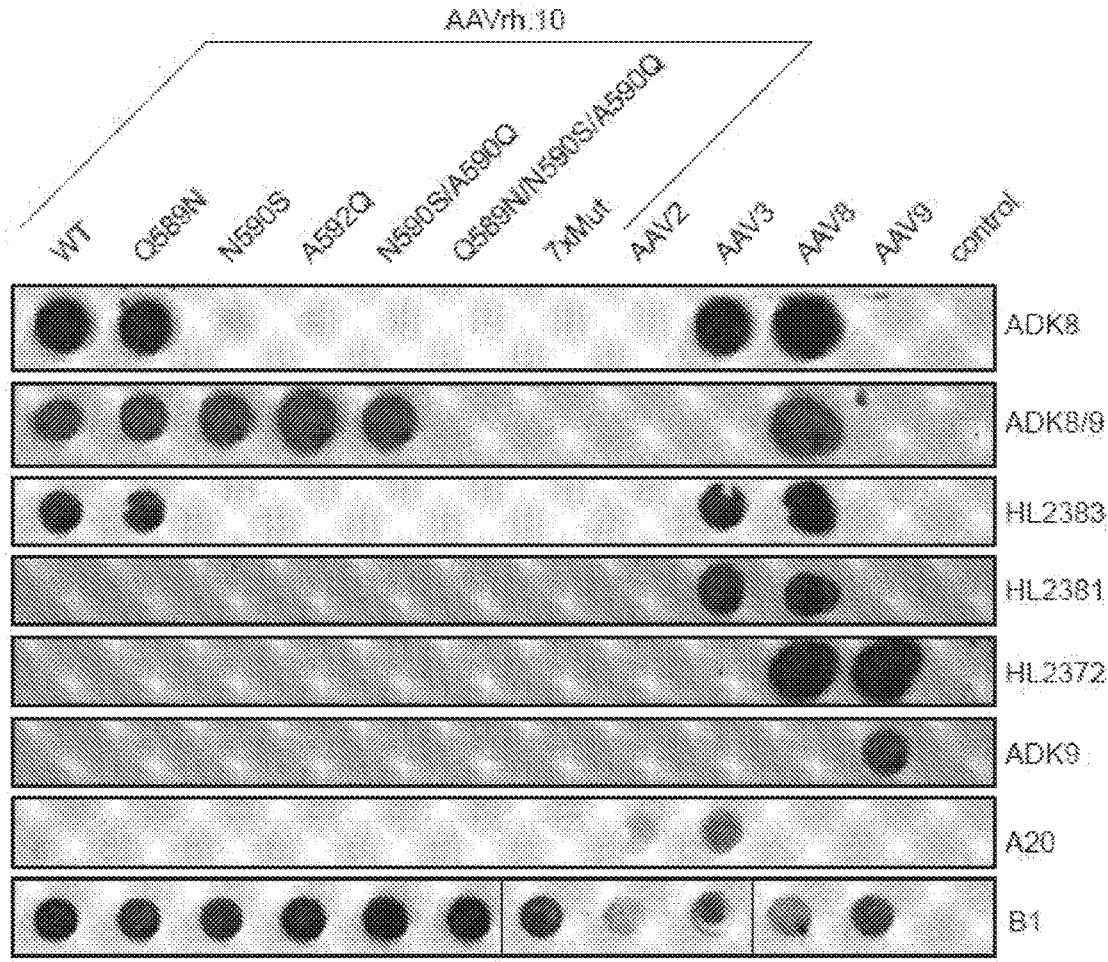
Figure 16C:
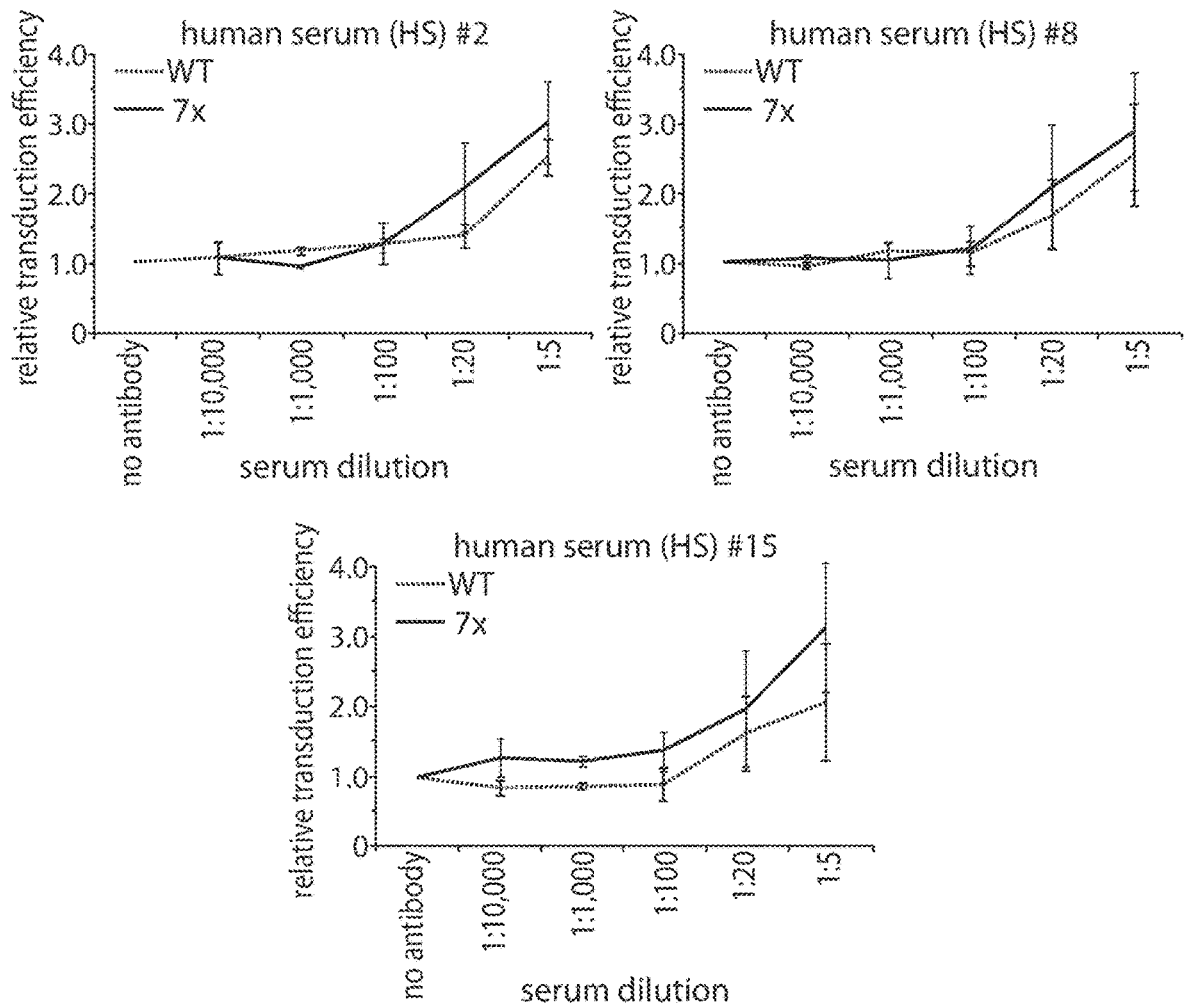
Figure 16D:
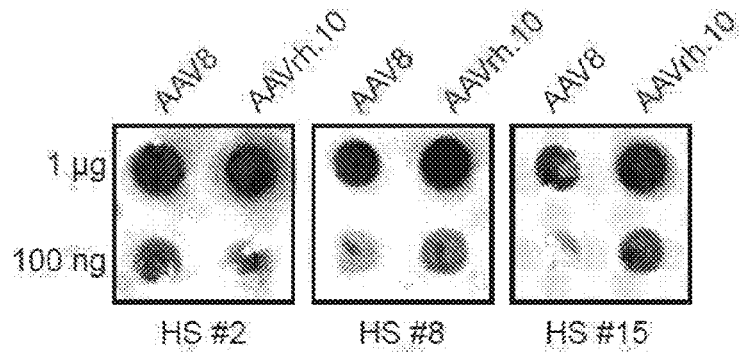

In some embodiments, a mutation in a capsid protein of a variant recombinant AAVrh.10 particle is a deletion (e.g., ΔS453). In some embodiments, a mutation is an amino acid substitution. In some embodiments, a substitution comprises an amino acid that is not present or conserved in one or more AAV particles of another serotype (e.g., AAV1, AAV2, AAV3, AAV4, AAV5, AAV6, AAV7, AAV8, AAV9, AAV10, AAV11, AAV12 or AAV13). In some embodiments, the other serotype may be an another AAV isolated from rhesus macaque tissue that is other than AAVrh.10. Gao et al (PNAS, 2003, 100:6081) discloses 37 capsid clones isolated from rhesus macaque tissues, and is incorporated herein by reference in its entirety. Non-limiting examples of conserved amino acid residues can be found in FIG. 5B, FIG. 5C and FIG. 10B. Sequences of other AAV serotypes are known and can be aligned with SEQ ID NO: 2 (wild type AAVrh.10 capsid protein) using techniques known in the art. In some embodiments, a substituted amino acid is not hydrophobic in nature.

Figure 3A:
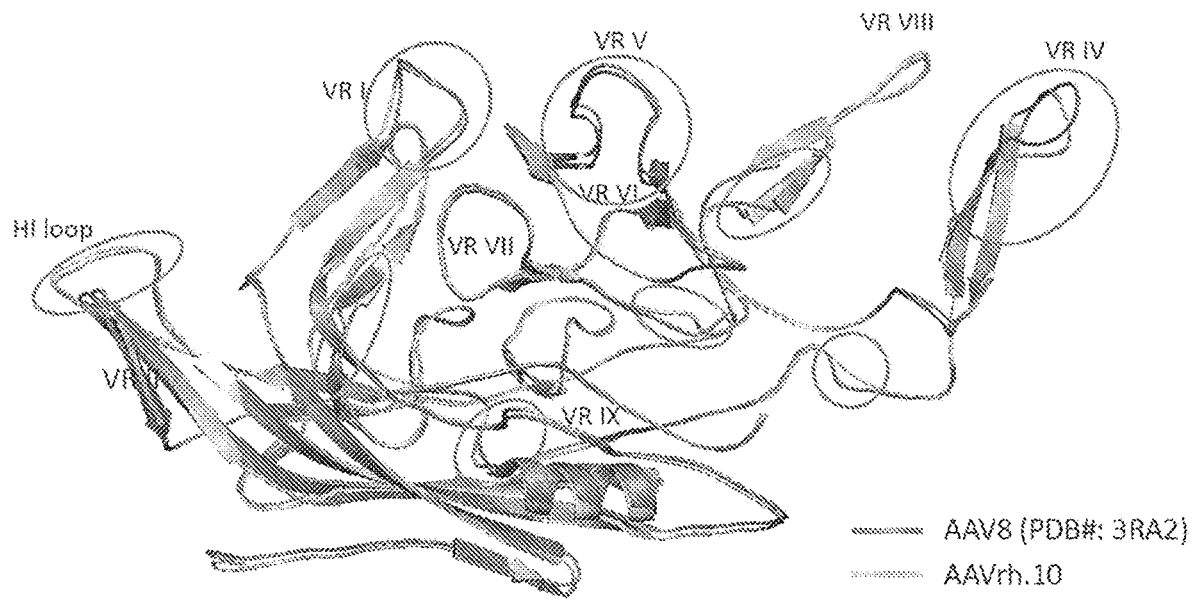
Figure 3B:
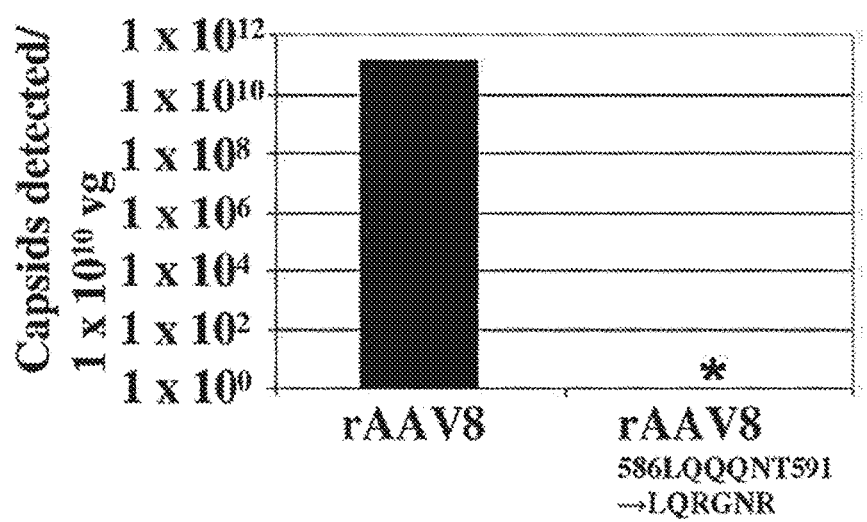

In some embodiments, a mutation in variant recombinant AAVrh.10 is on a capsid surface loop as depicted in FIG. 3A. A mutation in a variant rAAVrh.10 particle may be in any one of the surface loops depicted in FIG. 3A. The amino acid definition of these loops are listed in Table 1.

TABLE 1

Amino acid definition of AAVrh.10 capsid protein regions and loops

| AAVrh.10 VP regions/loops | Amino acid definition |
|---|---|
| VP1 complete | 1-738 |
| VP1u | 1-137 |

TABLE 1-continued

Amino acid definition of AAVrh.10 capsid protein regions and loops

| AAVrh.10 VP regions/loops | Amino acid definition |
|---|---|
| VP1/2 common region | 138-203 |
| VP3 | 204-738 |
| βB | 239-251 |
| βC | 280-287 |
| βD | 307-327 |
| βE | 343-349 |
| βF | 403-408 |
| βG | 410-419 |
| βH | 648-654 |
| βI | 676-691 |
| VR I | 263-271 |
| VR II | 329-333 |
| VR III | 383-391 |
| VR IV | 452-471 |
| VR V | 490-507 |
| VR VI | 528-544 |
| VR VII | 547-559 |
| VR VIII | 582-597 |
| HI-loop | 655-675 |
| VR IX | 707-714 |

In some embodiments, a mutation is at any one of the amino acid positions selected from the group consisting of: K259, K333, S453, S501, S559, Q589, N590, A592, S671, T674, Y708 and T719.

Non-limiting examples of mutations at these amino acid positions are K259L, K333V, ΔS453, S501A, S559A, Q589N, N590S, A592Q, S671A, T674V, Y708A and T719V.

In some embodiments, mutations comprise substitutions with amino acid residues that are not found on AAV of other serotypes. FIG. 14 provides amino acid residues in AAV particles of other serotype in comparison to non-limiting examples of AAVrh.10 mutations.

In some embodiments, more than one mutations are present on a recombinant or engineered AAVrh.10 capsid (e.g., 1, 2, 3, 4, 5, 6, or 7 or more) mutations. Non-limiting examples of AARrh.10 particles with multiple mutations are provided in FIG. 12 and FIG. 13. It is to be understood that any one mutations provided in this disclosure can be combined with any other mutation provided herein. It is also to be understood that AAVrh.10 variants with multiple mutations provided herein are merely examples and are non-limiting. Any one of the mutations disclosed in any one variant AAVrh.10 particles having multiple mutations may exist as a single mutation in an engineered AAVrh.10 particle, or in combination with one or more of the other mutations disclosed here. For example, a recombinant AARrh.10 particle as disclosed herein may contain any one of the mutations K259L, K333V, ΔS453, S501A, S559A, Q589N, N590S, A592Q, S671A, T674V, Y708A, or T719V. A recombinant AARrh.10 particle as disclosed herein may contain more than one of any of the mutations K259L, K333V, ΔS453, S501A, S559A, Q589N, N590S, A592Q, S671A, T674V, Y708A, or T719V. In some embodiments, a recombinant AARrh.10 particle as disclosed herein comprises the mutations N590S and A592Q. In some embodiments, a recombinant AARrh.10 particle as disclosed herein comprises the mutations Q589N, N590S and A592Q. In some embodiments, a recombinant AARrh.10 particle as disclosed herein comprises the mutations ΔS453, S559A, Q589N, N590S, A592Q and T719V. In some embodiments, a recombinant AARrh.10 particle as disclosed herein comprises the mutations K259L, ΔS453, S559A, Q589N, N590S, A592Q and T719V. In some embodiments, a recombinant AARrh.10 particle as disclosed herein comprises the mutations Q589N, N590S, A592Q and T719V. FIG. 12 lists some non-limiting examples of variant AAVrh.10 particles and their observed phenotypes. FIG. 13 lists some non-limiting examples of variant AAVrh.10 particles and their predicted phenotypes.

Cross Reactivity of AAVrh.10 to Neutralizing Antibodies

A neutralizing antibody is an antibody that defends a cell from an antigen or infectious body by neutralizing any effect it has biologically. In some embodiments, a neutralizing antibody to which an engineered variant AAVrh.10 particle shows modulated reactivity compared to a wild type AAVrh.10 particle may be any neutralizing antibody that reacts to any AAV particle. In some embodiments, a neutralizing antibody is against AAVrh.10. In some embodiments, a neutralizing antibody is against an AAV particle of another serotype (e.g., AAV1, AAV2, AAV3, AAV4, AAV5, AAV6, AAV7, AAV8, AAV9, AAV10, AAV11, AAV12 or AAV13). In some embodiments, the other serotype may be an another AAV isolated from rhesus macaque tissue that is other than AAVrh.10. In some embodiments, an AAV of another serotype is AAV2, AAV3, AAV7, AAV8, AAV9 or AAV13. In some embodiments, an AAV of another serotype is AAV8.

In some embodiments, a neutralizing antibody to which an engineered variant AAVrh.10 particle shows modulated reactivity compared to wild type AAVrh.10 reacts to AAVs of more than one serotype (e.g., an antibody reacting to both AAV8 and AAV9). In some embodiments, an AAV other than AAVrh.10 is a hybrid AAV and comprises sequences from more than one AAV serotype.

In some embodiments, a neutralizing antibody is ADK8, ADK9, IVIG, HL2381 or HL2383.

In some embodiments, a mutation in a capsid protein of any one of the recombinant AAVrh.10 particles disclosed herein results in decreased reactivity to neutralizing antibodies compared to a wild type AAVrh.10 particle. In some embodiments, reactivity to neutralizing antibodies is decreased by 5-100% (e.g., 5-10, 10-20, 20-40, 40-60, 60-80, 80-90, 90-95, 95-98, 95-99, 95-99.9, 100, 10-100, 30-100, 60-100, 70-100 or 80-100%) compared to wild type AAVrh.10 particles.

Non-limiting examples of AAVrh.10 capsid protein mutations that result in antibody escape or decreased reactivity to neutralizing antibodies are provided in FIG. 12. Non-limiting examples of AAVrh.10 capsid protein mutations that are predicted to result in antibody escape or decreased reactivity to neutralizing antibodies are provided in FIG. 13. Further non-limiting examples can be found in the Examples.

Reactivity of a recombinant AAVrh.10 particle to a neutralizing antibody can be measured in one of numerous methods known in the art for measuring binding of a virus particle to a protein (e.g., dot blotting, surface plasmon resonance or biolayer interferometry). Neutralization of virus infectivity by antibodies is described by Klasse (Adv Biol. 2014; 2014: 157895).

Alteration of Transduction Efficiency by Mutations in a AAVrh.10 Capsid Protein

In some embodiments, one or more mutations in a capsid protein of an AAVrh.10 particle results in altered transduction efficiency. The term "transduction" as used herein refers to the entry of an AAV particle into a cell, and is equivalent to "infection" of a cell.

In some embodiments, the transduction efficiency is increased compared to the transduction efficiency of a wild type AAVrh.10 particle. In some embodiments, the transduction efficiency of a variant AAVrh.10 particle is increased 1.2-500 fold (e.g., 1.2-2, 1.5-3, 3-5, 5-10, 10-100, 100-250 or 200-500 fold) compared to the transduction efficiency of a wild type AAVrh.10 particle for the same type of cell. In some embodiments, the transduction efficiency of a variant AAVrh.10 particle is increased by 5-200% (e.g., 5-10, 10-30, 20-50, 50-100, 5-60 or 100-200%) compared to the transduction efficiency of a wild type AAVrh.10 particle for the same type of cell. Mutations in an AAVrh.10 capsid protein that result in increased transduction efficiency are shown in FIG. 12. Mutations in an AAVrh.10 capsid protein that are predicted to result in increased transduction efficiency are shown in FIG. 13.

In some embodiments, the transduction efficiency of a variant AAVrh.10 particle is decreased compared to the transduction efficiency of a wild type AAVrh.10 particle. In some embodiments, the transduction efficiency of a variant AAVrh.10 particle is decreased 1.2-500 fold (e.g., 1.2-2, 1.5-3, 3-5, 5-10, 10-100, 100-250 or 200-500 fold) compared to the transduction efficiency of a wild type AAVrh.10 particle for the same type of cell. In some embodiments, the transduction efficiency of a variant AAVrh.10 particle is decreased by 5-100% (e.g., 5-100, 5-10, 10-30, 20-50, 20-70, 50-100, 5-60, 20-80 or 80-100%) compared to the transduction efficiency of a wild type AAVrh.10 particle for the same type of cell. In some embodiments, a mutation that leads to decreased transduction efficiency is at Y708 of the AAVrh.10 capsid protein. In some embodiments, a mutation at Y708 of the AAVrh.10 capsid protein is Y708A.

In some embodiments, a mutation in a AAVrh.10 capsid protein does not alter the transduction efficiency of the variant AAVrh.10 particle harboring the mutation. For example, FIG. 12 shows that a S671A mutation does not change the transduction efficiency of the variant AAVrh.10 particle harboring the mutation compared to the transduction efficiency of a wild type AAVrh.10 particle.

In some embodiments, a recombinant AAVrh.10 particle as disclosed herein is an empty capsid. In some embodiments, any one of the recombinant AAVrh.10 particles disclosed herein comprises a recombinant nucleic acid (e.g., a rAAV genome). In some embodiments, the recombinant nucleic acid comprises a transgene. In some embodiments, the transgene is operably linked or operably connected to a promoter. Accordingly, in some embodiments, an rAAVrh.10 particle comprises a transgene encoding a gene of interest, wherein the transgene is encapsidated by the viral capsid.

In some embodiments, a gene of interest encodes a therapeutic protein. A therapeutic protein may be an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic proteins, a nuclease or other protein used for gene editing, an Fc-fusion protein, or an anticoagulant. Some non-limiting examples of a therapeutic protein are CUCLN2, hARSA and factor IX.

In some embodiments, a gene of interest encodes a detectable molecule. In some embodiments, a detectable molecule is a fluorescent protein, a bioluminescent protein, or a protein that provides color (e.g., β-galactosidase, β-lactamasses, β-glucuronidase and spheriodenone). In some embodiments, a detectable molecule is a fluorescent, bioluminescent or enzymatic protein or functional peptide or functional polypeptide thereof.

In some embodiments, fluorescent protein is a blue fluorescent protein, a cyan fluorescent protein, a green fluorescent protein, a yellow fluorescent protein, an orange fluorescent protein, a red fluorescent protein, or functional peptides or polypeptides thereof. A blue fluorescent protein may be azurite, EBFP, EBFP2, mTagBFP, or Y66H. A cyan fluorescent protein may be ECFP, AmCyan1, Cerulean, CyPet, mECFP, Midori-ishi Cyan, mTFP1, or TagCFP. A Green fluorescent protein may be AcGFP, Azami Green, EGFP, Emarald, GFP or a mutated form of GFP (e.g., GFP-S65T, mWasabi, Stemmer, Superfolder GFP, TagGFP, TurboGFP, and ZsGreen). A yellow fluorescent protein may be EYFP, mBanana, mCitrine, PhiYFp, TagYFP, Topaz, Venus, YPet, or ZsYellow1. An orange fluorescent protein may be DsRed, RFP, DsRed2, DsRed-Express, Ds-Red-monomer, Tomato, tdTomato, Kusabira Orange, mKO2, mOrange, mOrange2, mTangerine, TagRFP, or TagRFP-T. A red fluorescent protein may be AQ142, AsRed2, dKeima-Tandem, HcRed1, tHcRed, Jred, mApple, mCherry, mPlum, mRasberry, mRFP1, mRuby or mStrawberry.

In some embodiments, a detectable molecule is a bioluminescent protein, or functional peptide or polypeptide thereof. Non-limiting examples of bioluminescent proteins are firefly luciferase, click-beetle luciferase, *Renilla* luciferase, or luciferase from *Oplophorus gracilirostris*.

In some embodiments, a detectable molecule may be any polypeptide or protein that can be detected using methods known in the art. Non-limiting methods of detection are fluorescence imaging, luminescent imaging and bright filed imaging.

In some embodiments, a nucleic acid is provided, the nucleic acid comprising an expression construct containing a promoter operably linked to a coding sequence of a gene of interest. In some embodiments, a promoter is a natural promoter. In some embodiments, a promoter can be a truncated natural promoter. In some embodiments, a promoter can include an enhancer and/or basal promoter elements from a natural promoter. In some embodiments, a promoter can be or include elements from a CMV, a chicken beta actin, a desmin, or any other suitable promoter or combination thereof. In some embodiments, a promoter can be an engineered promoter. In some embodiments, a promoter is transcriptionally active in host cells. In some embodiments, a promoter is less than 1.6 kb in length, less than 1.5 kb in length, less than 1.4 kb in length, less than 1.3 kb in length, less than 1.2 kb in length, less than 1.1 kb in length, less than 1 kb in length, or less than 900 kb 900 bp in length.

A promoter is "operably linked" to a nucleotide sequence when the promoter sequence controls and/or regulates the transcription of the nucleotide sequence. A promoter may be a constitutive promoter, tissue-specific promoter, an inducible promoter, or a synthetic promoter.

For example, constitutive promoters of different strengths can be used. A nucleic acid vector described herein may include one or more constitutive promoters, such as viral promoters or promoters from mammalian genes that are generally active in promoting transcription. Non-limiting examples of constitutive viral promoters include the Herpes Simplex virus (HSV), thymidine kinase (TK), Rous Sarcoma Virus (RSV), Simian Virus 40 (SV40), Mouse Mammary Tumor Virus (MMTV), Ad E1A cytomegalovirus (CMV) promoters. Non-limiting examples of constitutive mammalian promoters include various housekeeping gene promoters, as exemplified by the β-actin promoter (e.g., chicken β-actin promoter) and human elongation factor-1 α (EF-1α) promoter. In some embodiments, chimeric viral/mammalian promoters may include a chimeric CMV/chicken beta actin (CBA, CB or CAG) promoters.

Inducible promoters and/or regulatory elements may also be contemplated for achieving appropriate expression levels of the protein or polypeptide of interest. Non-limiting examples of suitable inducible promoters include those from genes such as cytochrome P450 genes, heat shock protein genes, metallothionein genes, and hormone-inducible genes, such as the estrogen gene promoter. Another example of an inducible promoter is the tetVP16 promoter that is responsive to tetracycline.

Several promoters are publically available or described. For example, Ple155 promoter is available through Addgene plasmid repository (Addgene plasmid #29011) and is described in Scalabrino et al. (Hum Mol Genet. 2015, 24(21):6229-39). Ye et al. (Hum Gene Ther.; 27(1):72-82) describes a shorter version of this promoter called PR1.7. A Thy1 promoter construct is also available through Addgene plasmid repository (Addgene plasmid #20736). A GRM6 promoter construct is also available through Addgene plasmid repository (Addgene plasmid #66391). Guziewicz et al. (PLoS One. 2013 Oct. 15; 8(10):e75666) and Esumi et al (J Biol Chem. 2004, 279(18):19064-73) provide examples of the use of VMD2 promoter. Dyka et al. (Adv Exp Med Biol. 2014; 801: 695-701) describes cone specific promoters for use in gene therapy, including IRBP and IRBPe-GNAT2 promoter. The use of PR2.1 promoter has been demonstrated in Komáromy et al. (Gene Ther. 2008 July; 15(14):1049-55) and its characterization in Karim et al. (Tree Physiol. 2015 October; 35(10):1129-39). Aartsen et al. (PLoS One, 5(8): e12387) describes the use of GFAP promoter to drive GFP expression in Muller glial cells. Other examples of Muller glia specific promoters are RLBP1 and GLAST (Vázquez-Chona, Invest Ophthalmol Vis Sci. 2009, 50(8):3996-4003; Regan et al., Journal of Neuroscience, 2007, 27(25): 6607-6619).

Synthetic promoters are also contemplated herein. A synthetic promoter may comprise, for example, regions of known promoters, regulatory elements, transcription factor binding sites, enhancer elements, repressor elements, and the like.

It is to be understood that a promoter may be a fragment of any one of the promoters disclosed herein, or one that retains partial promoter activity (e.g., 10-90, 30-60, 50-80, 80-99 or 90-99.9% of the activity) of a whole promoter.

In some embodiments, an AAV genome is built of single-stranded deoxyribonucleic acid (ssDNA), which is either positive- or negative-sensed. At each end of the DNA strand is an inverted terminal repeat (ITR). Between the ITRs are two open reading frames (ORFs): rep and cap. The rep ORF is composed of four overlapping genes encoding Rep proteins required for the AAV life cycle. The cap ORF contains overlapping nucleotide sequences of capsid proteins: VP1, VP2 and VP3, which interact together to form a capsid of an icosahedral symmetry.

In some embodiments, the nucleic acid encoding the gene of interest (e.g., along with a promoter) can be inserted in between two ITS (e.g., by replacing one or more of the viral genes). Accordingly, in some embodiments, a gene of interest is flanked by inverted terminal repeats (ITRs), e.g., AAV ITRs, ITRs from AAVrh.10 or any other AAV serotype including but not limited to AAV2, 3, 4, 5, 6, 7, 8, or 9. In some embodiments, a recombinant rAAV particle comprises a nucleic acid vector, such as a single-stranded (ss) or self-complementary (sc) AAV nucleic acid vector. In some embodiments, the nucleic acid vector contains an expression construct as described herein and one or more regions comprising inverted terminal repeat (ITR) sequences (e.g., wild-type ITR sequences or engineered ITR sequences) flanking the expression construct. In some embodiments, the nucleic acid is encapsidated by a viral capsid.

Recombinant AAVrh.10 Particle Compositions

Provided herein is a composition comprising any one of the recombinant AAVrh.10 particles disclosed herein.

In some embodiments, any one of the compositions provided herein comprises a pharmaceutically acceptable carrier. The term "carrier" refers to a diluent, adjuvant, excipient, or vehicle with which the rAAV particle is administered to a subject. Such pharmaceutical carriers can be sterile liquids, such as water and oils, including those of petroleum oil such as mineral oil, vegetable oil such as peanut oil, soybean oil, and sesame oil, animal oil, or oil of synthetic origin. Saline solutions and aqueous dextrose and glycerol solutions can also be employed as liquid carriers. Non-limiting examples of pharmaceutically acceptable carriers include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, saline, syrup, methylcellulose, ethylcellulose, hydroxypropylmethylcellulose, polyacrylic acids, lubricating agents (such as talc, magnesium stearate, and mineral oil), wetting agents, emulsifying agents, suspending agents, preserving agents (such as methyl-, ethyl-, and propyl-hydroxy-benzoates), and pH adjusting agents (such as inorganic and organic acids and bases). Other examples of carriers include phosphate buffered saline, HEPES-buffered saline, and water for injection, any of which may be optionally combined with one or more of calcium chloride dihydrate, disodium phosphate anhydrous, magnesium chloride hexahydrate, potassium chloride, potassium dihydrogen phosphate, sodium chloride, or sucrose. Other examples of carriers that might be used include saline (e.g., sterilized, pyrogen-free saline), saline buffers (e.g., citrate buffer, phosphate buffer, acetate buffer, and bicarbonate buffer), amino acids, urea, alcohols, ascorbic acid, phospholipids, proteins (for example, serum albumin), EDTA, sodium chloride, liposomes, mannitol, sorbitol, and glycerol. USP grade carriers and excipients are particularly useful for delivery of rAAV particles to human subjects.

Typically, such compositions may contain at least about 0.1% of the therapeutic agent (e.g., rAAV particle) or more, although the percentage of the active ingredient(s) may, of course, be varied and may conveniently be between about 1 or 2% and about 70% or 80% or more of the weight or volume of the total formulation. Naturally, the amount of therapeutic agent(s) (e.g., rAAV particle) in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be designed.

Method of Delivering a Protein of Interest to a Subject

Subjects previously treated with AAV particles develop neutralizing antibodies against those particles. In such instances, treating the subject again with AAV particles that would react or even cross react with the developed neutralizing antibodies results in an unwanted antigenic response. Any one of the compositions comprising any one of the variant AAVrh.10 particles that can escape neutralizing antibodies, as described herein, would be useful as a vehicle for gene delivery in such instances. Accordingly, provided herein is a method of delivering a protein of interest to a subject, the method comprising administering to the subject a composition comprising any one of the AAVrh.10 particles disclosed herein. Such a method diminishes the immunogenic response to the administered AAVrh.10 particles used to deliver a therapeutic gene.

Provided herein, is also a method of reducing the antigenic response to AAVrh.10 particles administer to a subject. In some embodiments, the antigenic response to any one of the variant AAVrh.10 particles disclosed herein decreases by, 5-100% (e.g., 5-100, 5-10, 10-30, 20-50, 20-70, 50-100, 5-60, 20-80 or 80-100%) compared to the antigenic response to a wild type AAVrh.10 particle in the same or same type of subject. A same type of subject may have the same neutralizing antibodies.

In some embodiments, a subject is a mammal. In some embodiments, a mammalian subject is a human, a non-human primate, a dog, a cat, a hamster, a mouse, a rat, a pig, a horse, a cow, a donkey or a rabbit.

Herein, "administering" or "administration" means providing a material to a subject in a manner that is pharmacologically useful.

In certain circumstances it will be desirable to deliver the rAAV particles in suitably formulated pharmaceutical compositions disclosed herein either subcutaneously, intraocularly, intravitreally, subretinally, parenterally, intravenously (IV), intracerebro-ventricularly, intramuscularly, intrathecally (IT), intracisternally, orally, intraperitoneally, by oral or nasal inhalation, or by direct injection to one or more cells, tissues, or organs by direct injection. In some embodiments, the administration is a route suitable for systemic delivery, such as by intravenous injection.

In some embodiments, the concentration of rAAV particles administered to a subject may be on the order ranging from $10^6$ to $10^{14}$ particles/ml or $10^3$ to $10^{15}$ particles/ml, or any values therebetween for either range, such as for example, about $10^6$, $10^7$, $10^8$, $10^9$, $10^{10}$, $10^{11}$, $10^{12}$, $10^{13}$, or $10^{14}$ particles/ml. In some embodiments, rAAV particles of a higher concentration than $10^{13}$ particles/ml are administered. In some embodiments, the concentration of rAAV particles administered to a subject may be on the order ranging from $10^6$ to $10^{14}$ vector genomes (vgs)/ml or $10^3$ to $10^{15}$ vgs/ml, or any values therebetween for either range (e.g., $10^6$, $10^7$, $10^8$, $10^9$, $10^{10}$, $10^{11}$, $10^{12}$, $10^{13}$, or $10^{14}$ vgs/ml). In some embodiments, rAAV particles of higher concentration than $10^{13}$ vgs/ml are administered. The rAAV particles can be administered as a single dose, or divided into two or more administrations as may be required to achieve therapy of the particular disease or disorder being treated. In some embodiments, 0.0001 ml to 10 mls are delivered to a subject. In some embodiments, the number of rAAV particles administered to a subject may be on the order ranging from $10^6$-$10^{14}$ vg/kg, or any values therebetween (e.g., $10^6$, $10^7$, $10^8$, $10^9$, $10^{10}$, $10^{11}$, $10^{12}$, $10^{13}$, or $10^{14}$ vgs/mg). In some embodiments, the dose of rAAV particles administered to a subject may be on the order ranging from $10^{12}$-$10^{14}$ vgs/kg. In some embodiments, the volume of rAAVrh.10 composition delivered to a subject (e.g., via one or more routes of administration as described herein) is 0.0001 mL to 10 mLs.

Vectors and Kits Useful in the Preparation of AAVrh.10 Particles

In some embodiments, provided herein is a vector comprising a nucleic acid encoding one or more AAVrh.10 Cap proteins with any one or more of the mutations described herein. Such a vector can be used to prepare or package any one of the AAVrh.10 particles disclosed herein. In some embodiments, provided herein is a vector comprising a nucleic acid encoding one or more genes of interest and/or one or more promoters. In some embodiments, a vector is a plasmid. In some embodiments, a vector (e.g., a plasmid) is provided in a host cell.

Methods of producing rAAV particles are known in the art (see, e.g., Zolotukhin et al. Production and purification of serotype 1, 2, and 5 recombinant adeno-associated viral vectors. Methods 28 (2002) 158-167; and U.S. Patent Publication Numbers US20070015238 and US20120322861, which are incorporated herein by reference; and plasmids and kits available from ATCC and Cell Biolabs, Inc.). For example, a plasmid comprising a gene of interest may be combined with one or more helper plasmids, e.g., that contain a rep gene (e.g., encoding Rep78, Rep68, Rep52 and Rep40) and transfected into recombinant cells such that the recombinant AAV particle can be packaged and subsequently purified.

In some embodiments, the one or more helper plasmids include a first helper plasmid comprising a rep gene, a nucleic acid encoding any one of the Cap proteins disclosed herein, and a second helper plasmid comprising one or more of the following helper genes: E1a gene, E1b gene, E4 gene, E2a gene, and VA gene. For clarity, helper genes are genes that encode helper proteins E1a, E1b, E4, E2a, and VA.

In some embodiments, the packaging is performed in a helper cell or producer cell, such as a mammalian cell or an insect cell. Non-limiting examples of mammalian cells are HEK293 cells, COS cells, HeLa cells, BHK cells, or CHO cells (see, e.g., ATCC® CRL-1573™, ATCC® CRL-1651™, ATCC® CRL-1650™, ATCC® CCL-2, ATCC® CCL-10™, or ATCC® CCL-61™). A non-limiting example of an insect cell is Sf9 cells (see, e.g., ATCC® CRL-1711™). A helper cell may comprises rep genes that encode the Rep proteins for use in a method described herein. In some embodiments, the packaging is performed in vitro.

Provided herein is also a kit that comprises tools for the preparing of any one of the AAVrh.10 particles provided herein. Such a kit comprises any one of the vectors encoding any one of the AAVrh.10 Cap proteins described herein, as a first component. A kit may also comprise a vector comprising AAV helper genes as a second component, wherein each component is packaged in separate containers. In some embodiments, a kit also comprises AAV packaging cells that are provided in a third container that is separate from the first and second containers.

Without further elaboration, it is believed that one skilled in the art can, based on the above description, utilize the present disclosure to its fullest extent. The following specific embodiments are, therefore, to be construed as merely illustrative, and not limitative of the remainder of the disclosure in any way whatsoever. All publications cited herein are incorporated by reference for the purposes or subject matter referenced herein.

EXAMPLES

Example 1: Solving the Structure of AAVrh.10 Particles

Structural Analysis

Figure 2A:
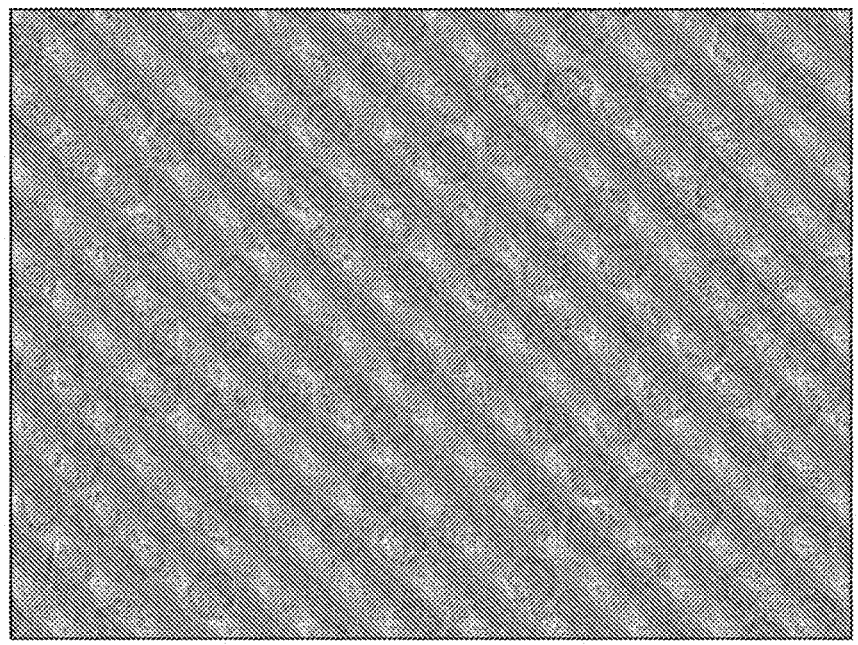
FIGS. 2A-2B show the AAVrh.10 structure obtained by cryo-electron microscopy (EM) and image reconstruction.
Figure 2B:
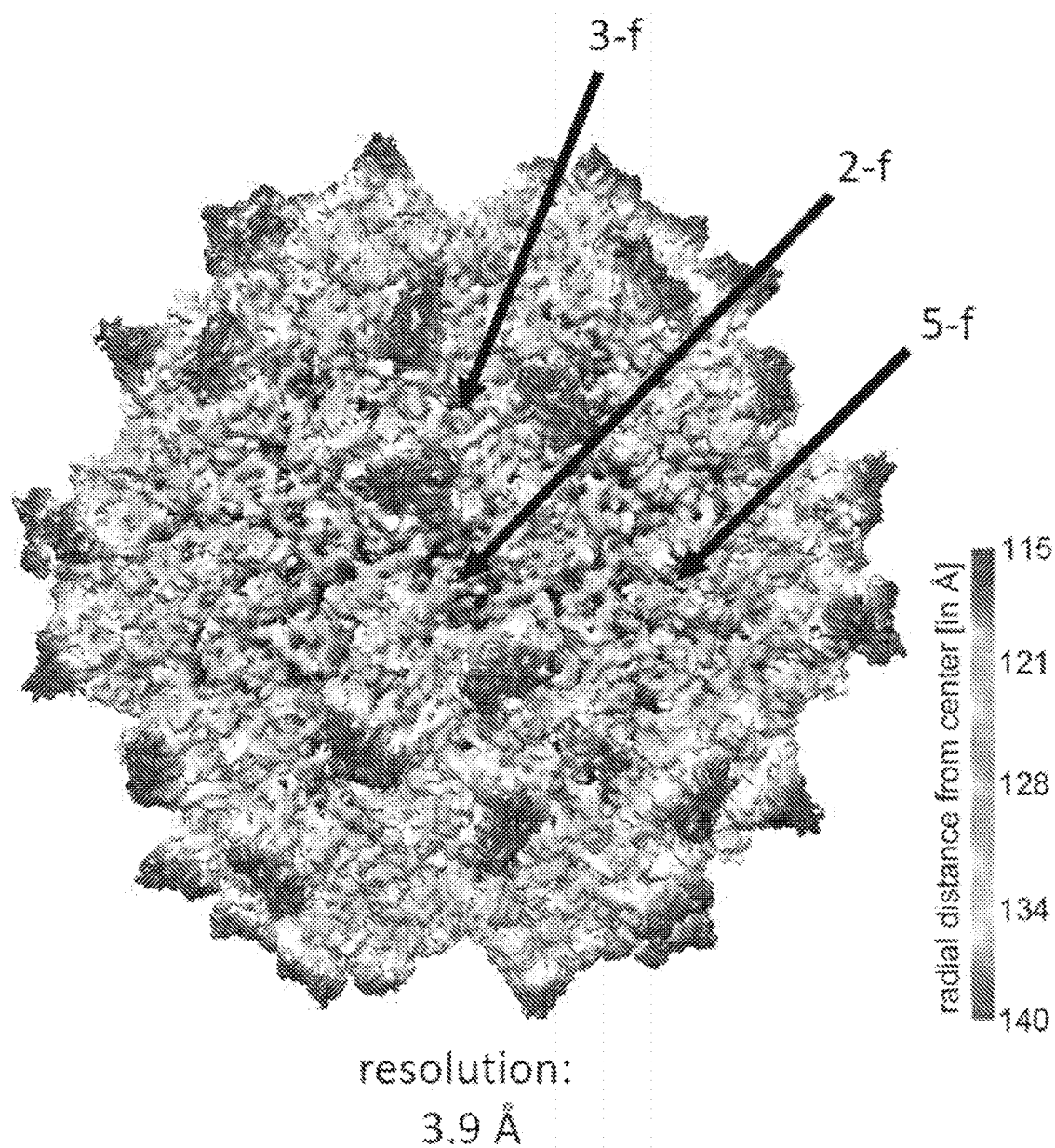

As mentioned above, information about the structure of AAVrh.10 particles was not previously known. To this end, cryo-electron microscopy (cryo-EM) and image reconstruction was therefore used to solve the structure of AAVrh.10 capsids. FIG. 2A and FIG. 2B show the surface topology of the solved structure. It was observed that AAVrh.10 exhibits the surface topology conserved in all AAVs, including depressions at the 2-fold axis, cylindrical channel at the 5-fold axis, and three protrusions around the 3-fold axis.

Thereafter, a structural alignment was performed comparing the capsid protein VP3 of AAVrh.10 to VP3 of AAV8, which has 92.5% sequence identity to VP3 of AAVrh.10. The AAV8 VP3 information can be found in the protein data base (PDB #: 3RA2). FIG. 3A shows the alignment of AAVrh.10 VP3 to AAV8 VP3.

A more thorough analysis was then performed on the VR VIII loop as shown in FIGS. 3A and 3C, and which contains the biding epitope on AAV8 to neutralizing antibody ADK8. It can be seen in FIG. 3C that AAVrh.10 aligns quite well with AAV8 in this region.

Antibody Recognition

Figure 4:
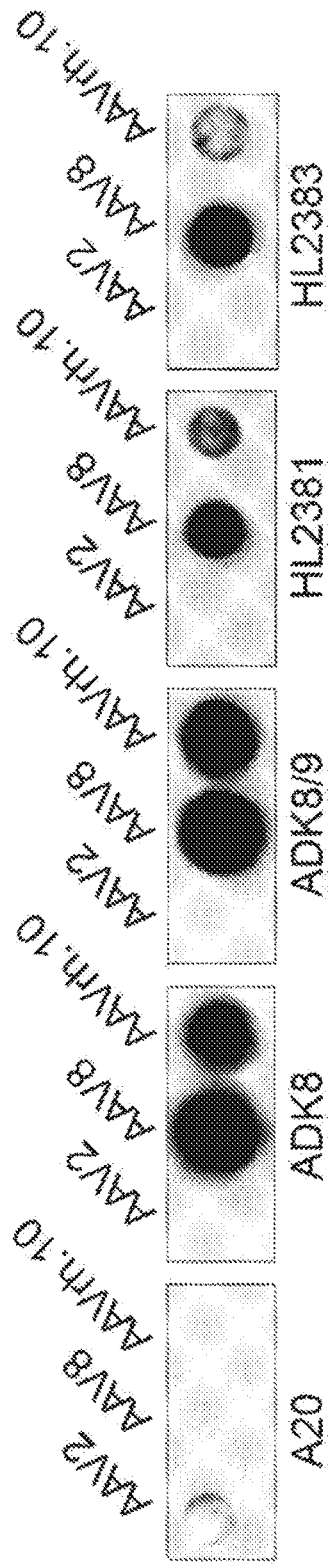
FIG. 4 shows antibody recognition of AAV2, AAV8 and AAVrh.10 capsids by native dot blot analysis. Black dots represent recognition while blank regions indicate lack of recognition. A20 was used as a negative control antibody. ADK8, ADK8/9, HL2381, and HL2383 are antibodies developed for AAV8 capsids. All of the AAV8-antibodies cross-react with AAVrh.10.

There are no known antibodies specific for AAVrh.10. However, given the close alignment of AAV8 and AAVrh.10 (FIG. 3C), experiments were conducted to assess the antibody recognition of AAVrh.10 by antibodies known to react with AAV8. FIG. 4 shows that antibodies against AAV8 (e.g., ADK8, ADK8/9, HL2381 and HL2383) cross-react with AAVrh.10.

Summary

The experimental data described in this example provides the basis for designing and engineering AAVrh.10 variants with mutations that might decrease the cross-reactivity to neutralizing antibodies.

Example 2: Generation of AAVrh.10 Antibody Escape Mutants

Based on the structural information described in Example 1, numerous mutations in AAVrh.10 capsid proteins were designed and tested for binding to cross-reacting neutralizing antibodies (FIG. 5A).

FIG. 5B and FIG. 5C show the amino acid sequence of the ADK8 and ADK8/9 epitopes, respectively. Based on the conserved residues among AAV serotypes that bind and do not bind to ADK8, mutations were made at positions N590 and A592 (FIG. 5B). Based on the conserved residues among AAV serotypes that bind and do not bind to ADK8/9, an additional mutation were made at position Q589 (FIG. 5C). FIGS. 5D-5F show the antibody escape phenotype variant AAVrh.10 particles with single and multiple mutations made in AAVr.10. It was found that the variant AAVrh.10 with N590S and A592Q mutations has reduced reactivity to antibodies ADK8, ADK8/9 and HL2383 (FIG. 5D and FIG. 5E). AAVrh.10 with mutations Q589N, N590S and A592Q also showed diminished reactivity to ADK8 and ADK8/9 (FIG. 5F).

Further determination of the antigenicity of the AAVrh.10 capsid is shown in FIG. 15. FIG. 15A shows immune-dot blot analysis of native rAAV capsids of indicated serotypes. $10^{10}$ genome-containing particles were spotted on a nitrocellulose membrane. The membranes were incubated with a panel of mAbs as depicted to the left of the membrane. Monoclonal antibody B1 served as an internal loading control. FIGS. 15B and 15C show sequence alignments for the VR-VIII loop of a selection of AAV serotypes (SEQ ID NOs: 16-22 from top to bottom, respectively). Amino acids highlighted in light grey indicate sequence identity among the AAVs. In addition amino acids highlighted in darker grey indicate common residues (FIG. 15B) among the ADK8 binding AAV serotypes in the ADK8 binding epitope and (FIG. 15C) among the ADK8/9 binding AAV serotypes in the ADK8/9 binding epitope. FIG. 15D The relative positions of seven mutations (7× mut) introduced into the VP proteins of AAVrh.10 are shown. FIG. 15E Comparison of the transduction of AAVrh.10 wild-type vectors to the generated AAVrh.10 7× mutant in HEK 293 cells by a luciferase assay (MOI 100,000).

Prevention of antibody-mediated AAVrh.10 neutralization is shown in FIG. 16. FIGS. 16A and 16B show a neutralization assay using increasing amounts of purified monoclonal antibodies, ADK8 in (FIG. 16A) and ADK8/9 in (FIG. 16B) with purified AAVrh.10 wild-type (dark grey) or 7× mut (light grey) vectors carrying a luciferase gene (MOI 100,000). FIG. 16C shows a similar neutralization assay as in (FIG. 16A) except that different human serum samples were used instead of monoclonal antibodies. FIG. 16D shows native dot blot analysis using the human serum samples used in (FIG. 16C) as primary antibodies on AAV8 and AAVrh.10.

Example 3: Identification of AAVrh.10 Cellular Receptor and Receptor Binding Site on the Capsid Surface As discussed above, very little is known about AAVrh.10, including what the cell-surface receptors are that are involved in transduction or infection of a cell by the AAVrh.10 particle. To gain some insight into this infection process, experiments were carried out to first tease out potential receptors, and then determine what the receptor binding site/s are on the AAVrh.10 capsid surface.

Identification of AAVrh.10 Receptor

FIGS. 6A and 6B show that the receptor for AAVrh.10 is not a heparan sulphate proteoglycans (HSPG), sialic acid or a terminal galactose. Data in FIG. 6A were obtained by carrying out transduction of cells in the presence of molecules that would block potential receptors from binding to AAVrh.10.

While a glycan array was initially found to be inconclusive (FIG. 6B), a closer analysis of data from a previously performed Consortium for Functional Glycomics (CFG) array, using a lower threshold for calling hits, found that AAVrh.10 bound to certain glycoaminoglycans, particularly those containing N-acetyllactosamine (LacNAc) [FIGS. 7A and 7B].

Upon further screening of AAVs on LacNAc glycan array, it was found that AAVrh.10 binds to sulfated LacNAc and that 6S N-acetyl-glucosamine is required for this binding (FIGS. 8A and 8B).

Identification of the Receptor Binding Site by Cryo-EM

Cryo-EM and image reconstruction of complexed AAVrh.10 capsid with excess LacNAc glycan molecules (#6, ~1 kDa) at a ratio of 100 glycan molecules per VP monomer was performed. FIG. 9A shows the cryo-EM reconstruction of AAVrh.10 complexed with LacNAc glycan. A subtraction was then carried out between the AAVrh.10 density map from the AAVrh.10 complexed with glycan to uncomplexed AAVrh.10. FIG. 9B shows the resultant difference map revealing additional density at the surface of the 2-fold symmetry axis.

Thereafter, an analysis of the conserved amino acids in the identified region was performed to determine amino acid residues necessary for receptor binding (FIG. 10A). It was found that Y708 was the only residue that is not conserved in all AAV serotypes (FIG. 10B). In further experiments testing cell transduction, it was observed that a Y708A mutation lead to reduced transduction of cells as assessed by transduction and expression of luciferase (FIG. 10C).

Effect of AAVrh.10 Mutations on Transduction Efficiency

FIG. 11 shows that all variant AAVrh.10 particles tested did not show diminished transduction efficiency, and in fact, most, with the exception of S671A, showed increased transduction efficiency. Cells were transduced with wild type and engineered variant AAVrh.10 particles comprising a gene encoding luciferase.

Summary

The information of which capsid surface region and which amino acid residues are necessary for binding to LacNAc receptors can be used to avoid generating mutations that would detrimentally affect cell transduction by variant AAVrh.10 particles compared to wild type AAVrh.10 particles.

OTHER EMBODIMENTS

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present disclosure, and without departing from the spirit and scope thereof, can make various changes and modifications of the disclosure to adapt it to various usages and conditions. Thus, other embodiments are also within the claims.

EQUIVALENTS

While several inventive embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive embodiments described herein. It is, therefore, to be understood that the foregoing embodiments are presented by way of example only and that, within the scope of the appended claims and equivalents thereto, inventive embodiments may be practiced otherwise than as specifically described and claimed. Inventive embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

All definitions, as defined and used herein, should be understood to control over dictionary definitions, definitions in documents incorporated by reference, and/or ordinary meanings of the defined terms.

All references, patents and patent applications disclosed herein are incorporated by reference with respect to the subject matter for which each is cited, which in some cases may encompass the entirety of the document.

The indefinite articles “a” and “an,” as used herein in the specification and in the claims, unless clearly indicated to the contrary, should be understood to mean “at least one.”

The phrase “and/or,” as used herein in the specification and in the claims, should be understood to mean “either or both” of the elements so conjoined, i.e., elements that are conjunctively present in some cases and disjunctively present in other cases. Multiple elements listed with “and/or” should be construed in the same fashion, i.e., “one or more” of the elements so conjoined. Other elements may optionally be present other than the elements specifically identified by the “and/or” clause, whether related or unrelated to those elements specifically identified. Thus, as a non-limiting example, a reference to “A and/or B”, when used in conjunction with open-ended language such as “comprising” can refer, in one embodiment, to A only (optionally including elements other than B); in another embodiment, to B only (optionally including elements other than A); in yet another embodiment, to both A and B (optionally including other elements); etc.

As used herein in the specification and in the claims, “or” should be understood to have the same meaning as “and/or” as defined above. For example, when separating items in a list, “or” or “and/or” shall be interpreted as being inclusive, i.e., the inclusion of at least one, but also including more than one, of a number or list of elements, and, optionally, additional unlisted items. Only terms clearly indicated to the contrary, such as “only one of” or “exactly one of,” or, when used in the claims, “consisting of,” will refer to the inclusion of exactly one element of a number or list of elements. In general, the term “or” as used herein shall only be interpreted as indicating exclusive alternatives (i.e. “one or the other but not both”) when preceded by terms of exclusivity, such as “either,” “one of,” “only one of,” or “exactly one of.” “Consisting essentially of,” when used in the claims, shall have its ordinary meaning as used in the field of patent law.

As used herein in the specification and in the claims, the phrase “at least one,” in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase “at least one” refers, whether related or unrelated to those elements specifically identified. Thus, as a non-limiting example, “at least one of A and B” (or, equivalently, “at least one of A or B,” or, equivalently “at least one of A and/or B”) can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as “comprising,” “including,” “carrying,” “having,” “containing,” “involving,” “holding,”

"composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03. It should be appreciated that embodiments described in this document using an open-ended transitional phrase (e.g., "comprising") are also contemplated, in alternative embodiments, as "consisting of" and "consisting essentially of" the feature described by the open-ended transitional phrase. For example, if the disclosure describes "a composition comprising A and B", the disclosure also contemplates the alternative embodiments "a composition consisting of A and B" and "a composition consisting essentially of A and B".

The invention claimed is:

1. A recombinant adeno-associated virus rh.10 (rAAVrh.10) particle comprising a capsid protein comprising one or more mutations in positions selected from S387, ΔS453, S559, and T719, wherein said mutations result in modulated reactivity to a neutralizing antibody and/or altered transduction efficiency relative to a wild-type AAVrh.10 particle having a capsid protein with an amino acid sequence of SEQ ID NO: 2.

2. The rAAVrh.10 particle of claim 1, wherein the neutralizing antibody is against AAVrh.10.

3. The rAAVrh.10 particle of claim 1, wherein the neutralizing antibody is against AAV1, AAV2, AAV3, AAV4, AAV5, AAV6, AAV7, AAV8, AAV9, AAV10, AAV11, AAV12 or AAV13.

4. The rAAVrh.10 particle of claim 1, wherein the neutralizing antibody is ADK8, ADK8/9, IVIG, HL2381 or HL2383.

5. The rAAVrh.10 particle of claim 4, wherein the reactivity to neutralizing antibodies is decreased by 5-100% compared to wild type AAVrh.10 particles.

6. The rAAVrh.10 particle of claim 4, wherein the transduction efficiency is increased by 5-200% compared to wild type AAVrh.10 particles.

7. The rAAVrh.10 particle of claim 1, further comprising one or more mutations at amino acid positions selected from the group consisting of: K259, K333, S501, Q589, N590, A592, S671, T674, and Y708, wherein the mutated positions are identified relative to SEQ ID NO: 2.

8. The rAAVrh.10 particle of claim 7, wherein the one or more mutations are amino acid substitutions selected from the group consisting of: K259L, K333V, S501A, Q589N, N590S, A592Q, S671A, T674V, and Y708A.

9. The rAAVrh.10 particle of claim 7, wherein the one or more mutations are N590S and A592Q.

10. The rAAVrh.10 particle of claim 7, wherein the one or more mutations are Q589N, N590S and A592Q.

11. The rAAVrh.10 particle of claim 1, wherein the one or more mutations are S387A, ΔS453, S559A, and T719V.

12. The rAAVrh.10 particle of claim 1, further comprising a transgene comprising a gene of interest.

13. The rAAVrh.10 particle of claim 12, wherein the gene of interest encodes a therapeutic protein.

14. The rAAVrh.10 particle of claim 13, wherein the therapeutic protein is an antibody, a peptibody, a growth factor, a clotting factor, a hormone, a membrane protein, a cytokine, a chemokine, an activating or inhibitory peptide acting on cell surface receptors or ion channels, a cell-permeant peptide targeting intracellular processes, a thrombolytic, an enzyme, a bone morphogenetic protein, a nuclease or other protein used for gene editing, an Fc-fusion protein, or an anticoagulant.

15. A composition comprising a rAAVrh.10 particle of claim 1 and a pharmaceutically acceptable carrier.

16. A method of delivering a protein of interest to a subject, the method comprising administering to the subject a composition comprising the rAAVrh.10 particle of claim 13.

17. The rAAVrh.10 particle of claim 1, wherein the capsid protein of the rAAVrh.10 particle comprises 1, 2, 3, 4, 5, 6, or 7 mutations, relative to the wild-type AAVrh.10 particle having a capsid protein with the amino acid sequence of SEQ ID NO: 2.

18. A capsid protein of serotype AAVrh.10 comprising one or more mutations in amino acid positions consisting of: S387, S453, S559, Q589, N590, A592, and T719 of SEQ ID NO: 2.

19. The capsid protein of claim 18, wherein the one or more mutations are amino acid substitutions consisting of: S387A, ΔS453, S559A, Q589N, N590S, A592Q, and T719V.

* * * * *

SEQUENCE LISTING

```
<160> NUMBER OF SEQ ID NOS: 22

<210> SEQ ID NO 1
<211> LENGTH: 2217
<212> TYPE: DNA
<213> ORGANISM: Artificial Sequence
<220> FEATURE:
<223> OTHER INFORMATION: adeno-associated virus serotype rh.10

<400> SEQUENCE: 1
atggctgccg atggttatct tccagattgg ctcgaggaca acctctctga gggcattcgc      60
gagtggtggg acttgaaacc tggagcccccg aaacccaaag ccaaccagca aaagcaggac     120
gacggccggg gtctggtgct tcctggctac aagtacctcg gacccttcaa cggactcgac     180 aaggggagc ccgtcaacgc ggcggacgca gcggccctcg agcacgacaa ggcctacgac      240
cagcagctca aagcgggtga caatccgtac ctgcggtata accacgccga cgccgagttt     300
caggagcgtc tgcaagaaga tacgtctttt gggggcaacc tcgggcgagc agtcttccag     360
gccaagaagc gggttctcga acctctcggt ctggttgagg aaggcgctaa gacggctcct     420
ggaaagaaga gaccggtaga gccatcaccc cagcgttctc cagactcctc tacgggcatc     480
ggcaagaaag gccagcagcc cgcgaaaaag agactcaact ttgggcagac tggcgactca     540
gagtcagtgc ccgaccctca accaatcgga gaacccccg caggcccctc tggtctggga     600
tctggtacaa tggctgcagg cggtggcgct ccaatggcag acaataacga aggcgccgac     660
ggagtgggta gttcctcagg aaattggcat tgcgattcca catggctggg cgacagagtc     720
atcaccacca gcacccgaac ctgggccctc cccacctaca caaccacct ctacaagcaa     780 atctccaacg gacttcggg aggaagcacc aacgacaaca cctacttcgg ctacagcacc     840
ccctgggggt attttgactt taacagattc cactgccact tctcaccacg tgactggcag     900
cgactcatca caacaactg gggattccgg cccaagagac tcaacttcaa gctcttcaac     960
atccaggtca aggaggtcac gcagaatgaa ggcaccaaga ccatcgccaa taaccttacc    1020
agcacgattc aggtctttac ggactcggaa taccagctcc cgtacgtcct cggctctgcg    1080
caccagggct gcctgcctcc gttcccggcg gacgtcttca tgattcctca gtacgggtac    1140
ctgactctga acaatggcag tcaggccgtg ggccgttcct ccttctactg cctggagtac    1200
tttccttctc aaatgctgag aacgggcaac aactttgagt tcagctacca gtttgaggac    1260
gtgccttttc acagcagcta cgcgcacagc caaagcctgg accggctgat gaacccctc    1320 atcgaccagt acctgtacta cctgtctcgg actcagtcca cggaggtac cgcaggaact    1380 cagcagttgc tattttctca ggccgggcct aataacatgt cggctcaggc caaaaactgg    1440 ctacccggc cctgctaccg gcagcaacgc gtctccacga cactgtcgca aaataacaac    1500
agcaactttg cctggaccgg tgccaccaag tatcatctga atggcagaga ctctctggta    1560
aatcccggtg tcgctatggc aacccacaag gacgacgaag agcgatttt tccgtccagc    1620 ggagtcttaa tgtttgggaa acagggagct ggaaaagaca acgtggacta tagcagcgtt    1680
```

-continued

```
atgctaacca gtgaggaaga aattaaaacc accaacccag tggccacaga acagtacggc   1740
gtggtggccg ataacctgca acagcaaaac gccgctccta ttgtaggggc cgtcaacagt   1800
caaggagcct tacctggcat ggtctggcag aaccgggacg tgtacctgca gggtcctatc   1860
tgggccaaga ttcctcacac ggacggaaac tttcatccct cgccgctgat gggaggcttt   1920
ggactgaaac accgcctcc tcagatcctg attaagaata cacctgttcc cgcggatcct   1980
ccaactacct tcagtcaagc taagctggcg tcgttcatca cgcagtacag caccggacag   2040
gtcagcgtgg aaattgaatg ggagctgcag aaagaaaaca gcaaacgctg aacccagag    2100 attcaataca cttccaacta ctacaaatct acaaatgtgg actttgctgt taacacagat   2160
ggcacttatt ctgagcctcg ccccatcggc acccgttacc tcacccgtaa tctgtaa      2217
```

<210> SEQ ID NO 2
<211> LENGTH: 738
<212> TYPE: PRT
<213> ORGANISM: Artificial Sequence
<220> FEATURE:
<223> OTHER INFORMATION: adeno-associated virus serotype rh.10

<400> SEQUENCE: 2

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270
```

```
Asn Thr Tyr Phe Gly Tyr Ser Thr Pro Trp Gly Tyr Phe Asp Phe Asn
            275                 280                 285

Arg Phe His Cys His Phe Ser Pro Arg Asp Trp Gln Arg Leu Ile Asn
        290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
530                 535                 540

Phe Gly Lys Gln Gly Ala Gly Lys Asp Asn Val Asp Tyr Ser Ser Val
545                 550                 555                 560

Met Leu Thr Ser Glu Glu Ile Lys Thr Thr Asn Pro Val Ala Thr
                565                 570                 575

Glu Gln Tyr Gly Val Val Ala Asp Asn Leu Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
```

```
                690                 695                 700
Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu

<210> SEQ ID NO 3
<211> LENGTH: 9
<212> TYPE: PRT
<213> ORGANISM: Artificial Sequence
<220> FEATURE:
<223> OTHER INFORMATION: adeno-associated virus 2

<400> SEQUENCE: 3

Asn Leu Gln Arg Gly Asn Arg Gln Ala
1               5

<210> SEQ ID NO 4
<211> LENGTH: 9
<212> TYPE: PRT
<213> ORGANISM: Artificial Sequence
<220> FEATURE:
<223> OTHER INFORMATION: adeno-associated virus 3

<400> SEQUENCE: 4

Asn Leu Gln Ser Ser Asn Thr Ala Pro
1               5

<210> SEQ ID NO 5
<211> LENGTH: 9
<212> TYPE: PRT
<213> ORGANISM: Artificial Sequence
<220> FEATURE:
<223> OTHER INFORMATION: adeno-associated virus 7

<400> SEQUENCE: 5

Asn Leu Gln Ala Ala Asn Thr Ala Ala
1               5

<210> SEQ ID NO 6
<211> LENGTH: 9
<212> TYPE: PRT
<213> ORGANISM: Artificial Sequence
<220> FEATURE:
<223> OTHER INFORMATION: adeno-associated virus 8

<400> SEQUENCE: 6

Asn Leu Gln Gln Gln Asn Thr Ala Pro
1               5

<210> SEQ ID NO 7
<211> LENGTH: 9
<212> TYPE: PRT
<213> ORGANISM: Artificial Sequence
<220> FEATURE:
<223> OTHER INFORMATION: adeno-associated virus serotype rh.10

<400> SEQUENCE: 7

Asn Leu Gln Gln Gln Asn Ala Ala Pro
1               5

<210> SEQ ID NO 8
<211> LENGTH: 9
<212> TYPE: PRT
```

```
<213> ORGANISM: Artificial Sequence
<220> FEATURE:
<223> OTHER INFORMATION: adeno-associated virus 13

<400> SEQUENCE: 8

Asn Leu Gln Asn Ser Asn Ala Gly Pro
1               5

<210> SEQ ID NO 9
<211> LENGTH: 9
<212> TYPE: PRT
<213> ORGANISM: Artificial Sequence
<220> FEATURE:
<223> OTHER INFORMATION: adeno-associated virus 9

<400> SEQUENCE: 9

Asn His Gln Ser Ala Gln Ala Gln Ala
1               5

<210> SEQ ID NO 10
<211> LENGTH: 31
<212> TYPE: PRT
<213> ORGANISM: Artificial Sequence
<220> FEATURE:
<223> OTHER INFORMATION: adeno-associated virus 1

<400> SEQUENCE: 10

Glu Val Gln Tyr Thr Ser Asn Tyr Ala Lys Ser Ala Asn Val Asp Phe
1               5                   10                  15

Thr Val Asp Asn Asn Gly Leu Tyr Thr Glu Pro Arg Pro Ile Gly
            20                  25                  30

<210> SEQ ID NO 11
<211> LENGTH: 31
<212> TYPE: PRT
<213> ORGANISM: Artificial Sequence
<220> FEATURE:
<223> OTHER INFORMATION: adeno-associated virus 2

<400> SEQUENCE: 11

Glu Ile Gln Tyr Thr Ser Asn Tyr Asn Lys Ser Val Asn Val Asp Phe
1               5                   10                  15

Thr Val Asp Thr Asn Gly Val Tyr Ser Glu Pro Arg Pro Ile Gly
            20                  25                  30

<210> SEQ ID NO 12
<211> LENGTH: 31
<212> TYPE: PRT
<213> ORGANISM: Artificial Sequence
<220> FEATURE:
<223> OTHER INFORMATION: adeno-associated virus 5

<400> SEQUENCE: 12

Glu Ile Gln Tyr Thr Asn Asn Tyr Asn Asp Pro Gln Phe Val Asp Phe
1               5                   10                  15

Ala Pro Asp Ser Thr Gly Glu Tyr Arg Thr Thr Arg Pro Ile Gly
            20                  25                  30

<210> SEQ ID NO 13
<211> LENGTH: 31
<212> TYPE: PRT
<213> ORGANISM: Artificial Sequence
<220> FEATURE:
<223> OTHER INFORMATION: adeno-associated virus 8

<400> SEQUENCE: 13
```

-continued

```
Glu Ile Gln Tyr Thr Ser Asn Tyr Tyr Lys Ser Thr Ser Val Asp Phe
1               5                   10                  15

Ala Val Asn Thr Glu Gly Val Tyr Ser Glu Pro Arg Pro Ile Gly
            20                  25                  30

<210> SEQ ID NO 14
<211> LENGTH: 31
<212> TYPE: PRT
<213> ORGANISM: Artificial Sequence
<220> FEATURE:
<223> OTHER INFORMATION: adeno-associated virus 9

<400> SEQUENCE: 14

Glu Ile Gln Tyr Thr Ser Asn Tyr Tyr Lys Ser Asn Asn Val Glu Phe
1               5                   10                  15

Ala Val Asn Thr Glu Gly Val Tyr Ser Glu Pro Arg Pro Ile Gly
            20                  25                  30

<210> SEQ ID NO 15
<211> LENGTH: 31
<212> TYPE: PRT
<213> ORGANISM: Artificial Sequence
<220> FEATURE:
<223> OTHER INFORMATION: adeno-associated virus serotype rh.10

<400> SEQUENCE: 15

Glu Ile Gln Tyr Thr Ser Asn Tyr Tyr Lys Ser Thr Asn Val Asp Phe
1               5                   10                  15

Ala Val Asn Thr Asp Gly Thr Tyr Ser Glu Pro Arg Pro Ile Gly
            20                  25                  30

<210> SEQ ID NO 16
<211> LENGTH: 14
<212> TYPE: PRT
<213> ORGANISM: Artificial Sequence
<220> FEATURE:
<223> OTHER INFORMATION: adeno-associated virus 2

<400> SEQUENCE: 16

Asn Leu Gln Arg Gly Asn Arg Gln Ala Ala Thr Ala Asp Val
1               5                   10

<210> SEQ ID NO 17
<211> LENGTH: 14
<212> TYPE: PRT
<213> ORGANISM: Artificial Sequence
<220> FEATURE:
<223> OTHER INFORMATION: adeno-associated virus 3

<400> SEQUENCE: 17

Asn Leu Gln Ser Ser Asn Thr Ala Pro Thr Thr Arg Thr Val
1               5                   10

<210> SEQ ID NO 18
<211> LENGTH: 14
<212> TYPE: PRT
<213> ORGANISM: Artificial Sequence
<220> FEATURE:
<223> OTHER INFORMATION: adeno-associated virus 7

<400> SEQUENCE: 18

Asn Leu Gln Ala Ala Asn Thr Ala Ala Gln Thr Gln Val Val
1               5                   10
```

```
<210> SEQ ID NO 19
<211> LENGTH: 14
<212> TYPE: PRT
<213> ORGANISM: Artificial Sequence
<220> FEATURE:
<223> OTHER INFORMATION: adeno-associated virus 8

<400> SEQUENCE: 19

Asn Leu Gln Gln Gln Asn Thr Ala Pro Gln Ile Gly Thr Val
1               5                   10

<210> SEQ ID NO 20
<211> LENGTH: 14
<212> TYPE: PRT
<213> ORGANISM: Artificial Sequence
<220> FEATURE:
<223> OTHER INFORMATION: adeno-associated virus serotype rh.10

<400> SEQUENCE: 20

Asn Leu Gln Gln Gln Asn Ala Ala Pro Ile Val Gly Ala Val
1               5                   10

<210> SEQ ID NO 21
<211> LENGTH: 14
<212> TYPE: PRT
<213> ORGANISM: Artificial Sequence
<220> FEATURE:
<223> OTHER INFORMATION: adeno-associated virus serotype rh.8

<400> SEQUENCE: 21

Asn Asn Gln Ala Ala Asn Thr Gln Ala Gln Thr Gly Leu Val
1               5                   10

<210> SEQ ID NO 22
<211> LENGTH: 14
<212> TYPE: PRT
<213> ORGANISM: Artificial Sequence
<220> FEATURE:
<223> OTHER INFORMATION: adeno-associated virus 9

<400> SEQUENCE: 22

Asn His Gln Ser Ala Gln Ala Gln Ala Gln Thr Gly Trp Val
1               5                   10
```